United States Patent [19]

Janssens et al.

[11] Patent Number: 4,588,722

[45] Date of Patent: May 13, 1986

[54] N-(4-PIPERIDINYL) BICYCLIC CONDENSED 2-IMIDAZOLAMINE DERIVATIVES

[75] Inventors: Frans E. Janssens, Bonheiden; Joseph L. G. Torremans, Beerse; Jozef F. Hens, Nijlen; Theophilus T. J. M. Van Offenwert, Vosselaar, all of Belgium

[73] Assignee: Janssen Pharmaceutica N.V., Beerse, Belgium

[21] Appl. No.: 660,670

[22] Filed: Oct. 15, 1984

Related U.S. Application Data

[63] Continuation-in-part of Ser. No. 569,115, Jan. 9, 1984, abandoned.

[51] Int. Cl.$^4$ ............................................ A61K 31/445
[52] U.S. Cl. ....................... 514/228; 514/232; 514/237; 514/255; 514/274; 514/275; 514/303; 514/322; 544/282; 544/285; 544/310; 544/316; 544/331; 546/118; 546/199; 546/116; 546/196
[58] Field of Search ............... 546/199, 116, 196, 118; 544/282, 285, 310, 316, 331; 514/228, 232, 237, 255, 274, 275, 303, 322

[56] References Cited

U.S. PATENT DOCUMENTS 4219559  8/1980  Janssens et al. .................... 424/267

*Primary Examiner*—Paul R. Michl
*Assistant Examiner*—Alex H. Walker
*Attorney, Agent, or Firm*—Geoffrey G. Dellenbaugh

[57] ABSTRACT

Novel N-(4-piperidinyl) bicyclic condensed 2-imidazolamine derivatives having antihistaminic properties which compounds are useful in the treatment of allergic diseases.

9 Claims, No Drawings

N-(4-PIPERIDINYL) BICYCLIC CONDENSED 2-IMIDAZOLAMINE DERIVATIVES

CROSS-REFERENCE TO RELATED APPLICATIONS

This is a continuation-in-part of our co-pending application Ser. No. 569,115 filed Jan. 9, 1984, now abandoned.

BACKGROUND OF THE INVENTION

In U.S. Pat. No. 4,219,559 there are described a number of N-heterocyclyl-4-piperidinamines having the formula

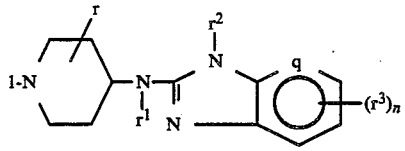

which compounds are useful as antihistaminic agents.

The compounds of the present invention differ from the prior art compounds essentially by the nature of the 1-piperidinyl substituent.

DESCRIPTION OF THE PREFERRED EMBODIMENTS

This invention is concerned with novel N-heterocyclyl-4-piperidinamines which may structurally be repesented by the formula

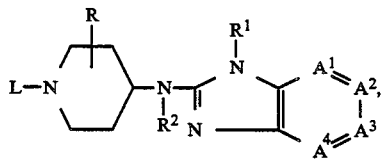

the pharmaceutically acceptable acid additions salts and the possible stereochemically isomeric forms thereof, wherein:

$A^1=A^2—A^3=A^4$ is a bivalent radical having the formula

wherein one or two hydrogen atoms in said radicals (a-1)–(a-5) may, each independently from each other, be replaced by halo, lower alkyl, lower alkyloxy, trifluoromethyl or hydroxy;

R is a member selected from the group consisting of hydrogen and lower alkyl;

$R^1$ is a member selected from the group consisting of hydrogen, alkyl, cycloalkyl, $Ar^1$ and lower alkyl substituted with one or two $Ar^1$ radicals;

$R^2$ is a member selected form the group consisting of hydrogen, lower alkyl, cycloalkyl, (lower alkyl)-CO-, (lower alkyl)OCO- and $Ar^2$-lower alkyl; and L is a radical of formula

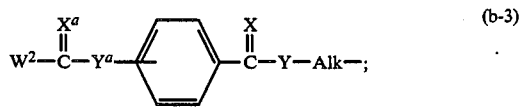

(lower alkenyl)—$Y^1$—Alk—; or (b-6)

(i) where $A^1=A^2—A^3=A^4$ is a radical of formula (a-3), (a-4) or (a-5), or (ii) where $A^1=A^2—A^3=A^4$ is a radical of formula (a-1) or (a-2), and $R^1$ is $Ar^3$ or lower alkyl substituted with one or two $Ar^3$ radicals, said $Ar^3$ being pyrazinyl, thiazolyl or imidazolyl, optionally substituted with lower alkyl: L may also be a radical of formula $Ar^1$-Alk- (b-7);

said W being a member selected from the group consisting of hydrogen, lower alkyl, $Ar^1$, $Ar^1$-lower alkyl, 1-piperidinyl, 1-pyrrolidinyl, 4-morpholinyl, a radical of formula

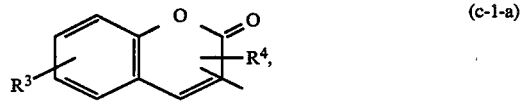

a radical of formula

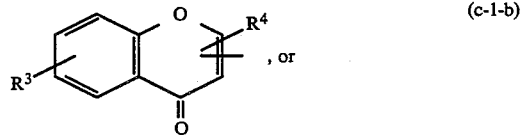

a radical of formula $W^1$-$Z^1$- (c-1-c), wherein $R^3$ and $R^4$ are each independently hydrogen or lower alkyl; and $W^1$ is cycloalkyl or lower alkyl, optionally substituted with up to two substituents selected from the group consisting of hydroxy, lower alkyloxy, 1-piperidinyl, 1-pyrrolidinyl, 4-morpholinyl and $Ar^1$; and where $Z^1$ is $NR^8$, $W^1$ may also be hydrogen, amino, lower alkylamino, $Ar^1$-amino or nitro;

said $W^2$ being a member selected from the group consisting of hydrogen, lower alkyl, $Ar^1$ and a radical of formula $R^5$-$Z^1$-(c-2-a), wherein $R^5$ is hydrogen, lower alkyl or $Ar^1$;

said T being a radical of formula

(c-3-a)

or $R^7—SO_2—NR^8—$ (c-3-b); $R^6$ being hydrogen, lower alkyl or $Ar^1$; $R^7$ being lower alkyl or $Ar^1$; and $R^8$ being hydrogen or lower alkyl;

said Het being a radical of formula (c-1-a), (c-1-b), or a radical of formula

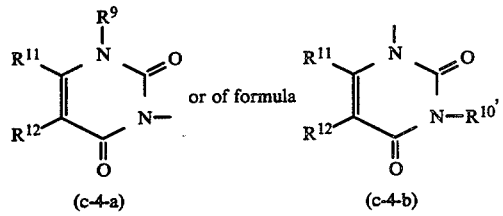

or a radical of formula

S being an integer wherein $R^9$, $R^{10}$, $R^{11}$ and $R^{12}$ are each independently hydrogen or lower alkyl; and wherein $R^{13}$ is hydrogen, lower alkyl or amino; or said Het being furan substituted with lower alkyl, said lower alkyl being optionally substituted with hydroxy, mercapto, lower alkyloxy, lower alkylthio, (aminolower alkyl)thio, $Ar^1$-O- or a radical of formula

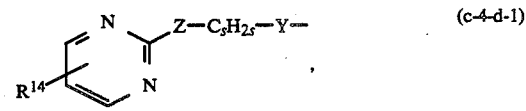

of from 1 to 6 inclusive; or where Z or Y is a direct bond, s may also be 0; and $R^{14}$ being hydrogen or lower alkyl; wherein:

n is 0 or the integer 1 or 2;
X is O, S, $NR^{15}$ or $CHNO_2$;
Y is O, S, $NR^{16}$ or a direct bond;
$Y^1$ is O, S or $NR^{16}$;
$Y^2$ is S or $NR^{16}$;
Z is O, S, $NR^8$ or a direct bond;
$Z^1$ is O, S or $NR^8$;
$X^a$ and $Y^a$ independently having the same meaning of X respectively Y;
said $R^{15}$ being hydrogen, lower alkyl, cyano, nitro, $Ar^2$-sulfonyl, lower alkylsulfonyl, lower alkylcarbonyl or $Ar^2$-carbonyl;
said $R^{16}$ being hydrogen, lower alkyl, ($Ar^2$)lower alkyl, 2-lower alkyloxy-1,2-dioxoethyl; or a radical of formula $—C(=X)—R^{17}$;
$R^{17}$ being hydrogen, lower alkyl, $Ar^2$, $Ar^2$-lower alkyl, lower alkyloxy, $Ar^2$-lower alkyloxy, mono- or di(lower alkyl)amino, $Ar^2$-lower alkylamino or $Ar^2$-lower alkyl(lower alkyl)amino; provided that:
(i) when $A^1=A^2—A^3=A^4$ is a radical of formula (a-1) or (a-2), and L is a radical of formula (b-1), wherein W is other than hydrogen or other than a radical of formula (c-1-a) or (c-1-b), then X is other than O;
(ii) when L is a radical of formula (b-1), wherein W is a radical of formula (c-1-c), wherein $Z^1$ is NH then $W^1$ is other than hydrogen or lower alkyl;
(iii) when $A^1=A^2—A^3=A^4$ is a radical of formula (a-1) or (a-2), and L is a radical of formula (b-3), wherein X is O, Y is $NR^{16}$, O or a direct bond, and $X^a$ is O,
(a) then $Y^a$ is not O;
(b) and $W^2$ being lower alkyl then $Y^a$ is not a direct bond;

wherein $Ar^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and lower alkyl-CO-; thienyl; halothienyl; furanyl; lower alkyl substituted furanyl; pyridinyl; pyrazinyl; thiazolyl and imidazolyl optionally substituted with lower alkyl; and wherein $Ar^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)-CO.

As used in the foregoing definitions the term halo is generic to fluoro, chloro, bromo and iodo; the term "lower alkyl" is meant to include straight- and branched-chain saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "alkyl" is meant to include lower alkyl radicals, as defined hereinabove, and the higher homologs thereof having from 7 to 10 carbon atoms; the term "cycloalkyl" is generic to cyclopropyl, cyclobutyl, cyclopentyl and cyclohexyl "lower alkenyl" is meant to include straight- or branched-chain hydrocarbon radicals containing one double bond, and having from 2 to 6 carbon atoms such as, for example, ethenyl, 2-propenyl, 2-butenyl, 3-pentenyl and 3-hexenyl, and the like; and "lower alkanediyl" is meant to include bivalent straight- or branched -chain alkanediyl radicals having from 1 to 6 carbon atoms.

Some of the compounds of formula (I) may contain in their structure a keto-enol tautomeric system or a vinylog system thereof and consequently these compounds may be present in their keto form as well as their enol form.

Preferred compounds within the invention are those wherein:
(i) L is a radical of formula (b-1), wherein Y is NH, X is O and W is hydrogen; or L is a radical of formula (b-1) wherein X is S, NH or NCN, Y is NH and W is 1-piperidinyl, 1-pyrrolidinyl, 4-morpholinyl, or a radical of formula (c-1-c), wherein $Z^1$ is $NR^8$ and $W^1$ is amino, nitro or lower alkyl, optionally substituted with one hydroxy, lower alkyloxy, 1-piperidinyl, 1-pyrrolidinyl, 4-morpholinyl or phenyl radical, or with two lower alkyloxy radicals; or L is a radical of formula (b-1), wherein X is S, NH or NCN, Y is NH and W is lower alkyloxy or lower alkylthio; or wherein L is a radical of formula (b-1) wherein W is a radical of formula (c-1-a) or (c-1-b);

(ii) L is a radical of formula (b-2) wherein n is 1, X is O or S and W is a radical of formula (c-1-c), wherein $Z^1$ is $NR^8$ and $W^1$ is lower alkyl;

(iii) L is a radical of formula (b-3), wherein X is O, Y is NH, $X^a$ is O, $Y^a$ is $NR^{15}$ and $W^2$ is lower alkyl;

(iv) L is a radical of formula (b-4), wherein T is a radical of formula (c-3-a), wherein X is O or S, Z is $NR^8$ and $R^6$ is hydrogen or lower alkyl; or wherein T is a radical of formula (c-3-b), wherein $R^8$ is hydrogen and $R^7$ is lower alkyl;

(v) L is a radical of formula (b-5) wherein Het is a radical of formula (c-4-a), wherein $R^9$, $R^{11}$ and $R^{12}$ are hydrogen; or wherein Het is a radical of formula (c-4-c); or wherein Het is furan substituted with lower alkyl bein substituted with hydroxy or with a radical of formula (c-4-d-1), wherein Y is O or S, Z is NH or a direct bond and $R^{14}$ is hydrogen;

(vi) L is a radical of formula (b-6) wherein $Y^1$ is O;

(vii) L is a radical of formula (b-7) wherein $Ar^1$ is phenyl substituted with hydroxy or lower alkyloxy.

In order to simplify the structural representations of the compounds of formula (I) and of certain precursors and intermediates thereof, the

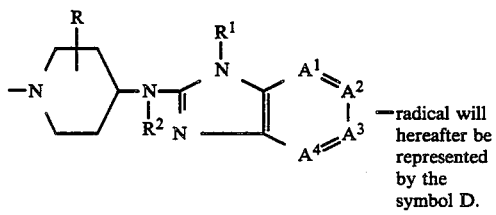

—radical will hereafter be represented by the symbol D.

The compounds of formula (I0 can generally be prepared by reacting an intermediate of formula (II) with a piperidine derivative of formula (III), following art-known alkylating procedures.

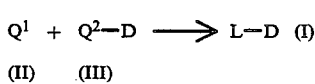

$Q^1$ and $Q^2$ are selected so that during the alkylation reaction a radical of formula L is formed. For example, the compound of formula (I) can generally be prepared by N-alkylating a piperidine of formula (III) wherein $Q^2$ is hydrogen, said piperidine being represented by the formula (III-a), with a reagent of formula (II) wherein $Q^1$ has the general formula L-G, (II-a).

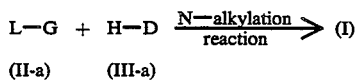

In (II-a) G represents an appropriate reactive leaving group such as, for example, halo, e.g., chloro, bromo or iodo, or a sulfonyloxy group, e.g. methylsulfonyloxy or 4-methylphenylsulfonyloxy.

Additionally, the compounds of formula (I) wherein L is a radical of formula (b-1) or (b-3) wherein Y is $Y^1$, or wherein L is a radical of formula (b-6) or (b-2), said compounds being represented by the formulae (I-a-1), respectively (I-a-2), (I-a-3) and (I-a-4) can be prepared by alkylating a piperidine of formula (III-b-1), respectively (III-b-2) with a reagent of formula (II-b-1) respectively (II-b-2), (II-b-3) and (II-b-4).

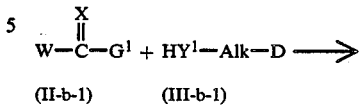

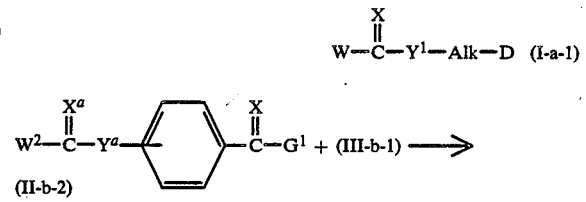

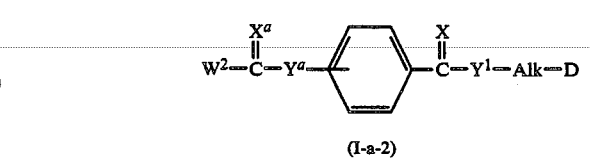

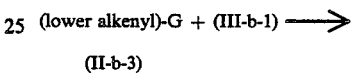

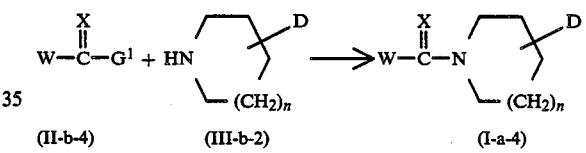

$G^1$ having the previously defined meaning of G and, where $G^1$ is connected to

it may also represent a lower alkyloxy, a lower alkylthio, and $Ar^2$-oxy, an $Ar^2$-thio, a lower alkylcarbonyloxy, or a lower alkyloxycarbonyloxy group, and where $G^1$ is connected to

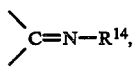

it may also be -N(lower alkyl)NO.

The compounds of formula (I-a-1), (I-a-2), (I-a-3), and the compounds of formula (I), wherein L is a radical or formula (b-5), wherein Het is a radical of formula (c-4-a), (c-4-b) or (c-4-c), said Het being represented by Het' and said compounds being represented by the formula (I-a-5), may also be prepared by alkylating a piperidine of formula (III), wherein $Q^2$ is a radical of formula -Alk-G, said piperidine being represented by the formula (III-c), with a reagent of formula (II-c-1), respectively (III-c-2), (II-c-3) and (II-c-4).

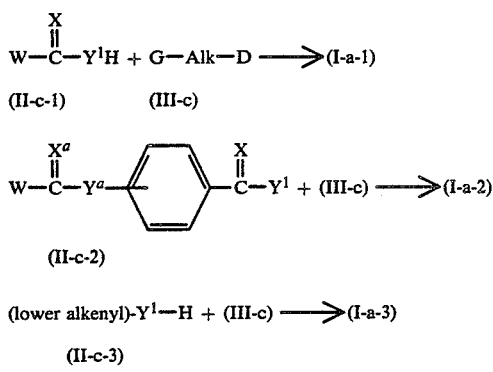

The compounds of formula (I-a-1) or (I-a-4), wherein W is $W^1$-$Z^1$-, said compounds being represented by the formula (Ia-1-a), respectively (I-a-4-a), may also be prepared by reacting a reagent of formula (II-d) with intermediate of formula (III-b-1) respectively (III-b-2) in the presence of an appropriate $$\diagdown\!\!\!\!\!C\!\!=\!\!X\diagup$$

generating agent such as, for example, urea, thiourea, 1,1'-carbonylbis[1H-imidazole], lower alkylcarbonohalidate, carbonyl chloride, thiocarbonyl chloride and the like.

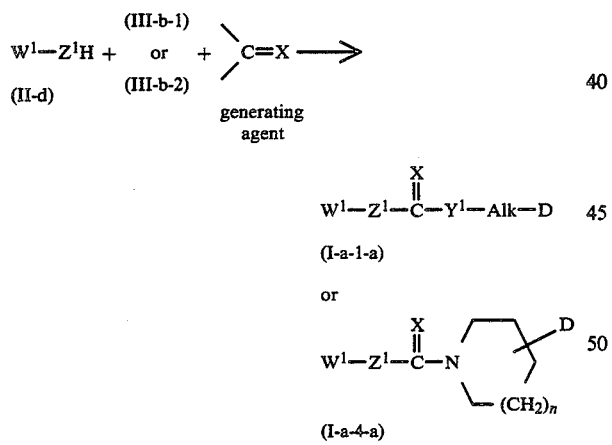

The alkylation reactions are conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

The compounds of formula (I) can also be prepared by the cyclodesulfurization reaction of an appropriate thiourea derivative of formula

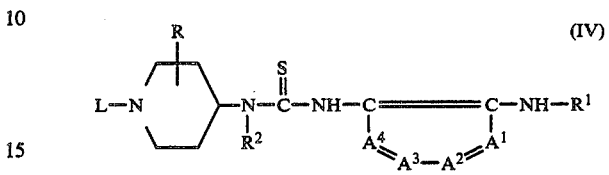

Said cyclodesulfurization reaction may be carried out by the reaction of (IV) with an appropriate alkyl halide, preferably iodomethane in an appropriate reaction-inert organic solvent, e.g., a lower alkanol such as methanol, ethanol, 2-propanol and the like. Otherwise, the cyclodesulfurization reaction may be carried out by the reaction of (IV) with an appropriate metal oxide or salt in an appropriate solvent according to art-known procedures. For example, the compounds of formula (I) can easily be prepared by the reaction of (IV) with an appropriate Hg(II) or Pb(II) oxide or salt, such as, for example HgO, $HgCl_2$, $Hg(OAc)_2$, PbO or $Pb(OAc)_2$. In certain instances it may be appropriate to supplement the reaction mixture with a small amount of sulfur. Even so methanediimines, especially N,N'-methanetetraylbis[cyclohexanamine] may be used as cyclodesulfurizing agents.

The compounds of formula (I), wherein L is a radical of formula (b-1), wherein Y is NH and X is O or S, said X being represented by $X^1$, and wherein W is a radical of formula (c-1-c), said compounds being represented by the formula (I-b-1), can generally be prepared by reacting an isocyanate or isothiocyanate of formula (VI) with a reagent of formula (V):

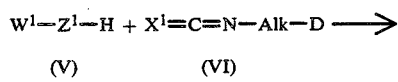

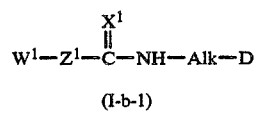

The compounds of formula (I), wherein L is a radical of formula (b-1), wherein Y is other than a direct bond, said Y being $Y^1$, X is $X^1$, and wherein W is a radical of formula (c-1-c), wherein $Z^1$ is NH, said compounds being represented by the formula (I-b-2), or the compounds of formula (I), wherein L is a radical of formula (b-2), wherein X is $X^1$, and wherein W is a radical of formula ( c-1-c), wherein $Z^1$ is NH, said compounds being represented by the formula (I-b-3), can be prepared by reacting an isocyanate or isothiocyanate of formula (VII) with an intermediate of formula (III-b-1), respectively (III-b-2).

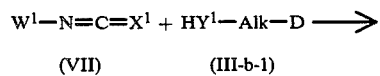

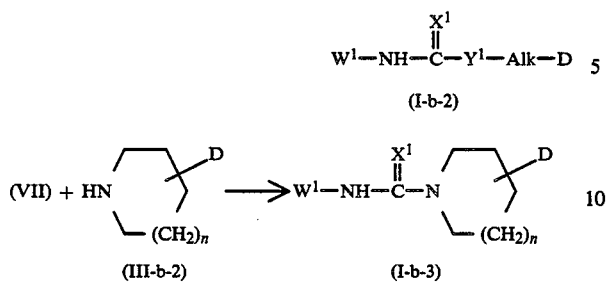

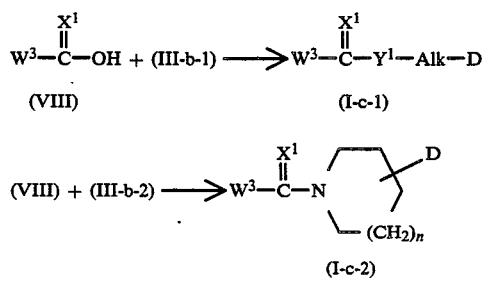

The reaction of (V) with (VI), of (VII) with (III-b-1) or (III-b-2) is generally conducted in a suitable reaction-inert solvent, such as, for example, an ether, e.g., tetrahydrofuran and the like. Elevated temperatures may be suitable to enhance the rate of the reaction. When $W^1$ is hydrogen, the reaction is conducted in aqueous medium containing an appropriate acid, such as, for example, acetic acid.

The compounds of formula (I) wherein L is a radical of formula (b-1), wherein Y is $Y^1$ and X is $X^1$ and wherein W is other than a radical of formula (c-1-c), said W being represented by $W^3$, and said compounds being represented by the formula (I-c-1), and the compounds of formula (I), wherein L is a radical of formula (b-2), wherein X is $X^1$ and W is $W^3$, said compounds being represented by the formula (I-c-2), may be prepared by reacting an intermediate of formula (III-b-1) respectively (III-b-2) with a reagent of formula (VIII).

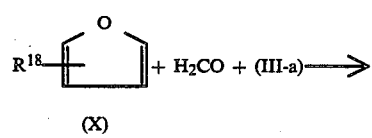

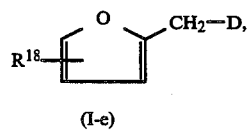

The reaction of (III-b-1) or (III-b-2) with (VIII) may generally be conducted following art-known esterification- or amidation reaction procedures. For example, the carboxylic acid may be converted into a reactive derivative, e.g., an anhydride or a carboxylic acid halide, which subsequently, is reacted with (III-b-1) or (III-b-2); or by reacting (III-b-1) or (III-b-2) and (VIII) with a suitable reagent capable of forming amides or esters, e.g., dicyclohexylcarbodiimide, 2-chloro-1-methylpyridinium iodide and the like. Said reactions are most conveniently conducted in a suitable solvent such as, for example, an ether, e.g. tetrahydrofuran, a halogenated hydrocarbon, e.g. dichloromethane, trichloromethane or a polar aprotic solvent, e.g. N,N-dimethylformamide. The addition of a base, e.g. N,N-diethylethanamine may be appropriate.

The compounds of formula (I) wherein L is a radical of formula (b-1), (b-3), (b-4), (b-5), (b-6) or (b-7), said compounds being represented by the formula (I-d), may also be prepared by reacting an appropriate alkenylene of formula (IX) with a piperidine of formula (III-a) by stirring and, if desired, heating the reactants together.

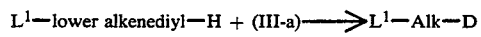

$L^1$ is selected so, that it forms, combined with -Alk-, a radical of formula (b-1), (b-3), (b-4), (b-5), (b-6) or (b-7).

The compounds of formula (I), wherein L is a radical of formula (b-5), wherein Alk is —$CH_2$—, wherein Het is a substituted 2-furanyl radical, said compounds being represented by the formula (I-e), can be prepared by reacting a substituted furan of formula (X) with an intermediate of formula (III-a) in the presence of formaldehyde or a polymeric form thereof in a suitable solvent.

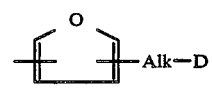

wherein $R^{18}$ is a previously described substituent of said furan ring.

The compounds of formula (I-e), wherein $R^{18}$ is a radical of formula (c-4-d-1), wherein Y is $Y^1$, said compounds being represented by the formula (I-e-1), or the compounds of formula (I-e), wherein $R^{18}$ is a radical of formula (c-4-d-1) wherein Z is $Z^1$, said compounds being represented by the formula (I-e-2), can be prepared by reacting an intermediate of formula (X-a), (X-b), (X-c) or (X-d) with a reagent of formula (XI-a), (XI-b), (XI-c) or (XI-d); in order to simplify the structural representation of the compounds of formula (I-e-1) and (I-e-2) and the intermediates of formula (X-a), (X-b), (X-c) and (X-d), the (lower alkyl)

radical will further be represented by the symbol $D^1$.

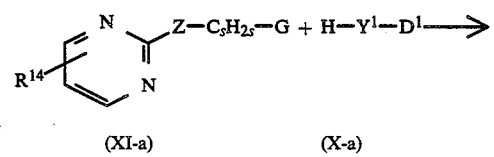

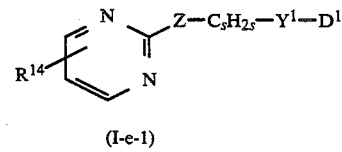

-continued

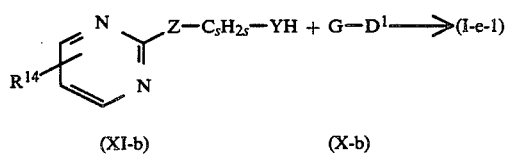

(XI-b)  (X-b)

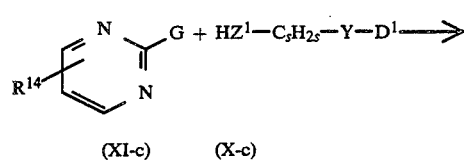

(XI-c)  (X-c)

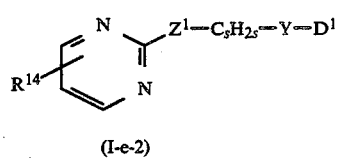

(I-e-2)

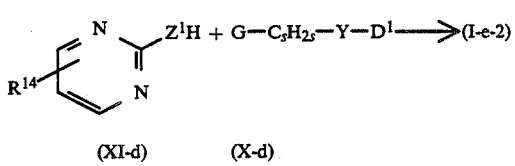

(XI-d)  (X-d)

The compounds of formula (I), wherein L is a radical of formula (b-3), wherein $Y^a$ is other than a direct bond, said $y^a$ being represented by $Y^{a-1}$, and said compounds by the formula (I-f-1), or wherein L is a radical of formula (b-4) wherein T is a radical of formula (c-3-a) or (c-3-b), said compounds being represented by the formula (I-f-2), respectively (I-f-3), can be prepared by reacting an intermediate of formula (XII-a), respectively (XII-b) and (XII-c), with a reagent of formula (XIII-a), respectively (XIII-b) and (XIII-c):

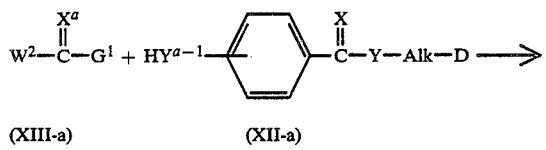

(XIII-a)  (XII-a)

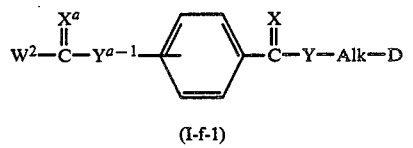

(I-f-1)

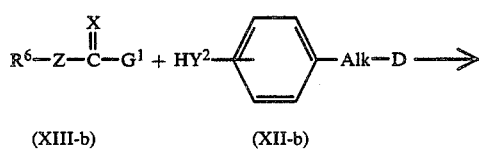

(XIII-b)  (XII-b)

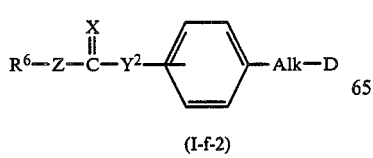

(I-f-2)

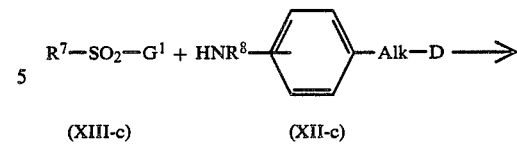

(XIII-c)  (XII-c)

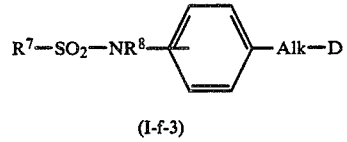

(I-f-3)

The reaction of the compounds of formulae (XI) with the compounds of formulae (X), and those of formulae (XIII) with those of formulae (XII) is conveniently conducted following the same procedures as described hereinabove for the synthesis from (I) starting from (II) and (III).

The compounds of formula (I), wherein L is a radical of formula (b-3), wherein $X^a$ is O or S, said $X^a$ being $X^{a-1}$, and wherein $Y^a$ is $Y^{a-1}$, and wherein $W^2$ is a radical of formula (c-2-a), wherein $Z^1$ is NH, said compounds being represented by the formula (I-g-1), and the compounds of formula (I), wherein L is a radical of formula (b-4), wherein T is a radical of formula (c-3-a), wherein X is $X^1$ and Z is NH, said compounds being represented by the formula (I-g-2), can be prepared by reacting a reagent of formula (XIV-a) respectively (XIV-b) with an intermediate of formula (XII-a) respectively (XII-b).

$R^5-N\!=\!C\!=\!X^{a-1}\,+$ (XIV-a)

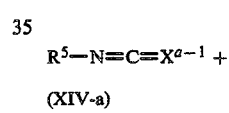

(XII-a)

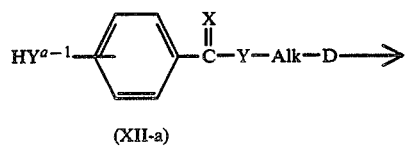

(I-g-1)

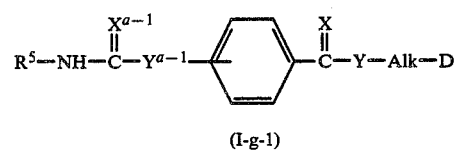

(XIV-b)  (XII-b)

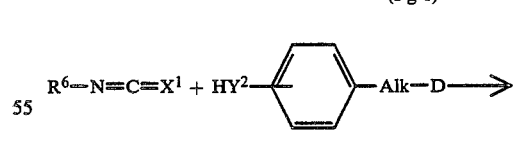

(I-g-2)

The reaction of the compounds of formula (XIV) with those of formula (XII) can conveniently be conducted following the same procedures as described hereinabove for the reaction of (V) with (VI), and (VII) with (III-b-1) or (III-b-2).

The compounds of formula (I) can also be converted into each other following art-known procedures of functional grouptransformation. Some examples will be cited hereinafter.

The compounds of formula (I) having a nitro substituent can be converted into their corresponding amines by stirring and, if desired, heating the starting nitrocompounds in a hydrogen-containing medium in the presence of a suitable amount of an appropriate catalyst such as, for example, platinum-on-charcoal, palladium-on-charcoal, Raney-nickel and the like catalysts. Suitable solvents are, for example, alcohols, e.g., methanol, ethanol and the like.

Halo atoms substituted on aryl groups may be replaced by hydrogen following art-known hydrogenolysis procedures, i.e. by stirring and, if desired, heating the starting compounds in a suitable solvent under hydrogen atmosphere in the presence of an appropriate catalyst, e.g., palladium-on-charcoal and the like catalysts. Said halo atoms may also be replaced by a lower alkyloxy or a lower alkylthio substituent by reacting the starting halo-compound with an appropriate alcohol or thioalcohol or, preferably, an alkali- or earth alkaline metal salt or an appropriate alcohol or thioalcohol in a suitable solvent. Said lower alkyloxy or alkylthio substituents may be converted into alcohol or thiol groups by hydrolysing the starting lower alkyloxy or alkylthio compounds in an acidic aqueous medium such as, for example, an aqueous hydrogen halide solution.

The compounds of formula (I), containing a Y, $Y^1$ or $Y^2$ group of formula NH can be converted into compounds of formula (I) wherein Y, $Y^1$ or $Y^2$ is $NR^{16}$, $R^{16}$ being other than hydrogen, by reacting the starting amine with an appropriate N-alkylating or N-acylating agent such as, for example, a lower alkyl or $Ar^2$-lower alkyl halogenide, e.g. bromomethane, iodoethane, (chloromethyl)benzene and the like; or a carboxylic acid or a derivative thereof, e.g. an acid halide, an acid anhydride and the like.

The compounds of formula (I), containing a Y, $Y^1$ or $Y^2$ group of formula $NR^{16}$, wherein $R^{16}$ is the previously described radical of formula $-C(=X)-R^{17}$, wherein X is O or S and $R^{17}$ is lower alkylamino, or $Ar^2$lower alkylamino can be prepared by reacting the starting amine with an appropriate isocyanate or isothiocyanate.

The compounds of formula (I) wherein L is a radical of formula (lower alkyl-O)$_2$

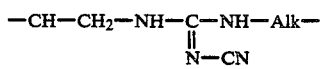

may be converted into compounds of formula (I) wherein L is a radical of formula

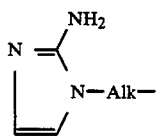

by reacting the former compounds with an appropriate acid in the presence of a suitable solvent, e.g. water.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

A number of intermediates and starting materials in the foregoing preparations are known compounds which may be prepared according to art-known methodologies of preparing said or similar compounds. A number of such preparation methods will be described hereinafter in more detail.

The intermediates of formula (III-a) can conveniently be prepared starting from a thiourea derivative of formula

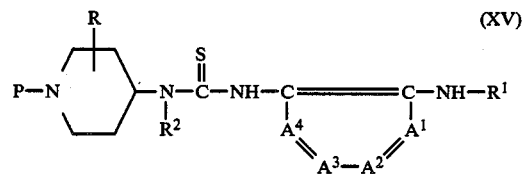

wherein P is an appropriate protective group such as, for example, lower alkyloxycarbonyl, $Ar^2-CH_2-O-CO-$, $Ar^2-CH_2-$ and the like, by a cyclodesulfurization reaction following the same procedure as described hereinabove for the preparation of (I) starting from (IV) and, subsequently eliminating the protective group P in the thus obtained intermediate of formula

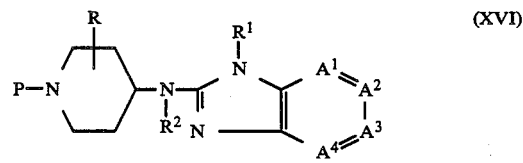

The elimination of the protective group P in (XVI) may generally be carried out following art-known procedures such as, for example, by hydrolysis in alkaline or acidic aqueous medium.

The intermediates of formula (III-b-1) and (III-c) may be derived from the corresponding intermediates of formula (III-a) by reacting the latter with a suitable reagent following art-known N-alkylating procedures. For example, intermediates of formula (III-b-1) wherein $HY^1$-Alk-represents a radical of formula $H_2N-CH_2$-Alk'-, (III-b-1-a), can also be prepared by reacting an intermediate of formula (III-a) with a nitrile of formula (XVII) following art-known N-alkylating procedures and subsequently converting the thus obtained nitrile (XVIII) into the corresponding amine (III-b-1-a) following art-known nitrile to amine reducing procedures, e.g., by catalytically hydrogenating procedures and the like.

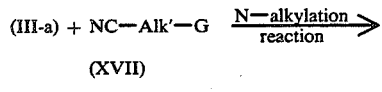

(XVII)

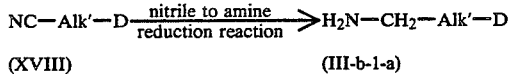

(XVIII)  (III-b-1-a)

In (XVII), (XVIII) and (III-b-1-a) Alk' has the same meaning as Alk provided that one methylene function is missing.

The intermediates of formula (III-b-1) wherein HY$^1$-Alk-represents a radical of formula HY$^1$—CH$_2$—CH$_2$—, (III-b-1-b), may also be prepared by the reaction of (III-a) with a reagent of formula (XIX) by stirring and, if desired, heating the reactants together in a suitable solvent.

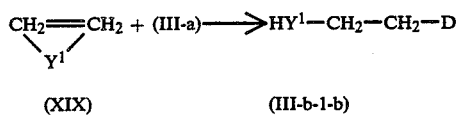

(XIX)  (III-b-1-b)

The intermediates of formula (III-b-1) may be converted into an intermediate of formula (III-c) by converting the function HY$^1$ into an appropriate leaving group, e.g., where Y$^1$ is O, said intermediates being represented by the formula (I-b-1-c) by converting a hydroxy function into a chloro atom, with thionyl chloride, phosphoryl chloride and the like.

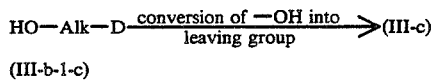

(III-b-1-c)

The intermediates of formula (III-b-1-a) may also be derived from an appropriate corresponding carbonyl-oxidated form by reacting said carbonyl-oxidated form with hydroxylamine and reducing the thus obtained oxime following art-known methods, e.g., catalytic hydrogenation and the like reducing methods.

The intermediates of formula (III-b-1) or (III-b-2) may also be prepared by reacting a reagent containing both a protected Y$^1$ or NH function and a carbonyl function, by reacting said reagent with (III-a) and reducing the thus obtained intermediate following art-known procedures, e.g. catalytic hydrogenation and the like, followed by an elimination reaction of the group protecting Y$^1$. For example, the intermediates of formula (III-b-2), wherein D is substituted by a 4-piperidinyl radical, said compounds being represented by the formula (III-b-2-a), can be prepared by reacting a reagent of formula (XX) with (III-a) followed by an appropriate reduction, and subsequently eliminating the protective group P as described hereinabove:

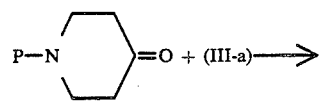

-continued

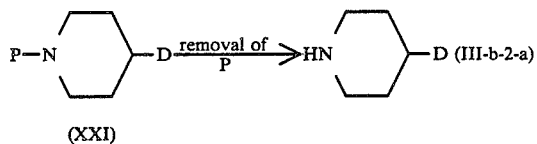

(XXI)

The intermediates of formula (IV) can conveniently be prepared by converting the amino group in the compounds of formula (III-b-1-a) into an isocyanato or isothiocyanato group following art-known procedures, for example, by reacting said amino group with CS$_2$ in the presence of ethyl carbonochloridate and the like.

The intermediates of formula (X-a) can be converted into intermediates of formula (X-b) by a suitable conversion of the Y$^1$H group into a leaving group; the intermediates of formula (X-c) wherein Y is other than a direct bond, said Y being Y$^1$, can also be prepared by alkylating (X-a) with an appropriate reagent; the intermediates of formula (X-c) can be converted into those of formula (X-d) by a suitable conversion of the Z$^1$H group into a leaving group.

The intermediates of formula (XII-a), wherein Y is other then a direct bond, can be prepared by alkylating an intermediate of formula (III-b-1) with an appropriate aromatic reagent; the intermediates of formula (XII-b) and (XII-c) can be prepared following art-known procedures as described in, for example, U.S. Pat. No. 4,219,559.

The intermediate of formula (XV) and those of formula (XV) wherein R$^2$ is hydrogen, (XV-a), may be prepared by reacting a piperidine of formula (XXII-a) or (XXII-b) with an aromatic reagent of formula (XXIII-a) or (XXIII-b).

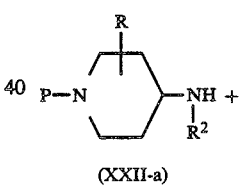

(XXII-a)

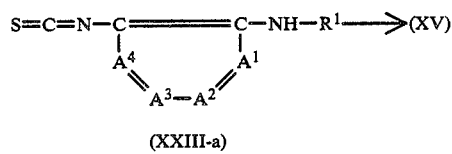

(XXIII-a)

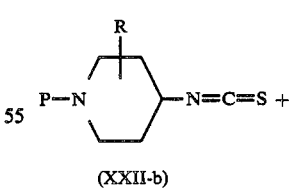

(XXII-b)

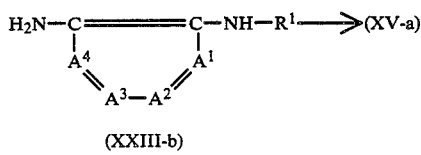

(XXIII-b)

During one of the reactions the intermediates wherein R$^1$ and/or R$^2$ and/or R$^8$ and/or R$^{15}$ and/or R$^{16}$ is hydrogen may be converted into the corresponding intermediates wherein $R^1$ and/or $R^2$ and/or $R^8$ and/or $R^{15}$ and/or $R^{16}$ is other than hydrogen following art-known N-alkylating, N-acylating or reductive N-alkylating procedures.

From formula (I) it is evident that the compounds of this invention may have several asymmetric carbon atoms in their structure. Each of these chiral centers may be present in a R- and a S-configuration, this R- and S-notation being in correspondence with the rules described by J. Org. Chem. 35 (9), 2849–2867 (1970).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodogies known to those skilled in the art.

Stereochemically isomeric forms of the compounds of formula (I) are naturally intended to be embraced within the scope of the invention.

The compounds of formula (I) have histamine antagonistic properties and some of the compounds of formula (I) have also serotoninantagonistic properties.

The useful antihistaminic properties of the compounds of formula (I) are demonstrated in the following test procedure.

PROTECTION OF RATS FROM COMPOUND 48/80-INDUCED LETHALITY

Compound 48/80, a mixture of oligomers obtained by condensation of 4-methoxy-N-methylbenzeneethanamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test compounds. Male rats of an inbred Wistar strain, weighing 240–260 g were used in the experiment. After overnight starvation the rats were transferred to conditioned laboratories (temp.=21±1° C., relative humidity=65±5%). The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration.

The $ED_{50}$-values of the compounds of formula (I) are listed in table 1. Said $ED_{50}$-values are the values in mg/kg body weight at which the tested compounds protect 50% of the tested animals against compound 48/80-induced lethality.

The compounds listed in table 1 are not given for the purpose of limiting the invention thereto but only to exemplify the useful pharmacological activities of all the compounds within the scope of the formula (I).

TABLE 1

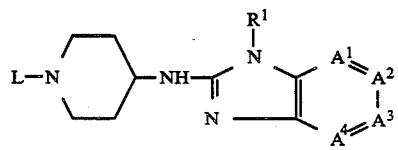

| Comp. No. | L | $R^1$ | $-A^1=A^2-A^3=A^4-$ | base or salt form | mp. °C. | Column 1 Compound 48/80 lethality test in rats-$ED_{50}$ in mg/kg body weight |
|---|---|---|---|---|---|---|
| 47 | HOCH₂—[furan]—CH₂ | 4-F—C₆H₄CH₂ | —CH=CH—CH=CH— | base | 148.8 | 0.08 |
| 50 | [pyridinyl]—NH(CH₂)₂SCH₂—[furan]—CH₂ | 4-F—C₆H₄CH₂ | —CH=CH—CH=CH— | base | 128.9 | 0.16 |
| 5 | [dihydropyrimidinedione]—N—CH₂—CH₂ | 4-F—C₆H₄CH₂ | —CH=CH—CH=CH— | base | 245.8 | 0.08 |

TABLE 1-continued

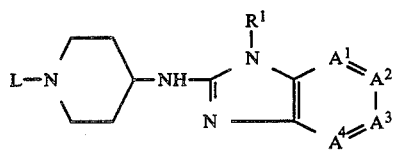

| Comp. No. | L | R¹ | —A¹=A²—A³=A⁴— | base or salt form | mp. °C. | Column 1 Compound 48/80 lethality test in rats-ED$_{50}$ in mg/kg body weight |
|---|---|---|---|---|---|---|
| 2 | 4-CH$_3$OC$_6$H$_4$(CH$_2$)$_2$ | 4-F—C$_6$H$_4$CH$_2$ | —CH=CH—CH=N— | base | 186.8 | 0.08 |
| 3 | 4-CH$_3$OC$_6$H$_4$(CH$_2$)$_2$ | 4-F—C$_6$H$_4$CH$_2$ | —CH=CH—N=CH— | base | 184.5 | 0.16 |
| 59 | 4-HOC$_6$H$_4$(CH$_2$)$_2$ | (4-thiazolyl)CH$_2$ | —CH=CH—CH=CH— | 2HBr | 291.0 | 0.08 |
| 13 | 4-CH$_3$OC$_6$H$_4$(CH$_2$)$_2$ | (2-pyrazinyl)CH$_2$ | —CH=CH—CH=CH— | base | 127.4 | 0.04 |
| 17 | 4-CH$_3$OC$_6$H$_4$(CH$_2$)$_2$ | (4-thiazolyl)CH$_2$ | —CH=CH—CH=CH— | 2HBr 2H$_2$O | 239.2 | 0.08 |
| 23 | HN=C—NH(CH$_2$)$_2$ <br> \| <br> NH—NO$_2$ | 4-F—C$_6$H$_4$CH$_2$ | —CH=CH—CH=CH— | base | 146.7 | 0.08 |
| 25 | (CH$_3$)$_2$N—C—NH(CH$_2$)$_2$ <br> \|\| <br> N—CN | 4-F—C$_6$H$_4$CH$_2$ | —CH=CH—CH=CH— | base | 110.5 | 0.08 |
| 24 | CH$_3$O—CHCH$_2$NHCNH(CH$_2$)$_2$ <br> \|          \|\| <br> CH$_3$O     N—CN | 4-F—C$_6$H$_4$CH$_2$ | —CH=CH—CH=CH— | (E)-2-butenedioate (1:2) | 173.1 | 0.16 |
| 21 | CH$_3$S—C—NH(CH$_2$)$_2$ <br> \|\| <br> N—CN | 4-F—C$_6$H$_4$CH$_2$ | —N=CH—CH=CH— | base | 172.2 | 0.16 |
| 26 | O⟨morpholino⟩N(CH$_2$)$_2$NHCNH(CH$_2$)$_2$ <br> \|\| <br> N—CN | 4-F—C$_6$H$_4$CH$_2$ | —CH=CH—CH=CH— | H$_2$O | 125.6 | 0.16 |
| 35 | (C$_2$H$_5$O)—C—NH(CH$_2$)$_2$ <br> \|\| <br> S | 4-F—C$_6$H$_4$CH$_2$ | —CH=CH—CH=CH— | base | 148.6 | 0.16 |
| 34 | H$_2$N—NH—C—NH(CH$_2$)$_2$ <br> \|\| <br> S | 4-F—C$_6$H$_4$CH$_2$ | —CH=CH—CH=CH— | H$_2$O | 183.8 | 0.02 |
| 40 | C$_6$H$_5$—NH—C—NH(CH$_2$)$_2$ <br> \|\| <br> S | 4-F—C$_6$H$_4$CH$_2$ | —CH=CH—CH=CH— | base | 162.7 | 0.16 |
| 28 | O⟨morpholino⟩N—C—NH(CH$_2$)$_2$ <br> \|\| <br> S | 4-F—C$_6$H$_4$CH$_2$ | —CH=CH—CH=CH— | base | 191.6 | 0.16 |
| 31 | (CH$_3$)$_2$NH—C—NH(CH$_2$)$_2$ <br> \|\| <br> S | 4-F—C$_6$H$_4$CH$_2$ | —CH=CH—CH=CH— | base | 159.7 | 0.08 |
| 32 | (C$_2$H$_5$)$_2$NH—C—NH(CH$_2$)$_2$ <br> \|\| <br> S | 4-F—C$_6$H$_4$CH$_2$ | —CH=CH—CH=CH— | base | 175.5 | 0.16 |
| 30 | HO(CH$_2$)$_3$NH—C—NH(CH$_2$)$_2$ <br> \|\| <br> S | 4-F—C$_6$H$_4$CH$_2$ | —CH=CH—CH=CH— | H$_2$O | 124.6 | 0.08 |

TABLE 1-continued

Structure: L—N(piperidine)—NH—C(=N—)—N(R¹)— fused to ring with A¹=A², A³=A⁴

| Comp. No. | L | R¹ | —A¹=A²—A³=A⁴— | base or salt form | mp. °C. | Column 1 Compound 48/80 lethality test in rats-ED₅₀ in mg/kg body weight |
|---|---|---|---|---|---|---|
| 36 | CH₃—NH—CO—N(piperidin-4-yl) | 4-F—C₆H₄CH₂ | —CH=CH—CH=CH— | H₂O | 152.4 | 0.16 |
| 37 | CH₃—NH—CS—N(piperidin-4-yl) | 4-F—C₆H₄CH₂ | —CH=CH—CH=CH— | base | 218.8 | 0.08 |
| 45 | HCO—NH—(CH₂)₂ | 4-F—C₆H₄CH₂ | —CH=CH—CH=CH— | base | 153.2 | 0.08 |
| 46 | HCO—NH—(CH₂)₂ | (2-furanyl)CH₂ | —CH=CH—CH=CH— | ½ H₂O | 125.2 | 0.16 |
| 56 | H₂N—CO—NH—C₆H₄—(CH₂)₂ | 4-F—C₆H₄CH₂ | —CH=CH—CH=CH— | base | 186.9 | 0.04 |
| 52 | (C₂H₅)N—Ac* / C₆H₄—CO—NH—(CH₂)₂ | 4-F—C₆H₄CH₂ | —CH=CH—CH=CH— | (E)-2-butene-dioate (1:2) | 175.2 | 0.31 |
| 51 | NH—Ac* / C₆H₄—CO—NH—(CH₂)₂ | 4-F—C₆H₄CH₂ | —CH=CH—CH=CH— | base | 170.9 | 0.16 |
| 1 | CH₂=CH—O—(CH₂)₂ | 4-F—C₆H₄CH₂ | —CH=CH—CH=CH— | base | 138.5 | 0.08 |
| 57 | CH₃—NH—CO—NH—C₆H₄—(CH₂)₂ | 4-F—C₆H₄CH₂ | —CH=CH—CH=CH— | base | 300 | 0.08 |
| 53 | CH₃SO₂NH—C₆H₄—(CH₂)₂ | 4-F—C₆H₄CH₂ | —CH=CH—CH=CH— | H₂O | 191.0 | 0.16 |
| 12 | 2-oxo-2H-chromen-3-yl—(CH₂)₂ | 4-F—C₆H₄CH₂ | —CH=CH—CH=CH— | base | 168.4 | 0.16 |
| 14 | 2-oxo-2H-chromen-3-yl—(CH₂)₂ | (2-furanyl)CH₂ | —CH=CH—CH=CH— | H₂O | 133.2 | 0.08 |

TABLE 1-continued $$L-N\underset{}{\diagdown}\text{NH}-\overset{R^1}{\underset{N}{\diagup}}\overset{A^1}{\underset{A^4}{\diagdown}}\overset{A^2}{\underset{A^3}{\diagup}}$$

| Comp. No. | L | $R^1$ | $-A^1=A^2-A^3=A^4-$ | base or salt form | mp. °C. | Column 1 Compound 48/80 lethality test in rats-$ED_{50}$ in mg/kg body weight |
|---|---|---|---|---|---|---|
| 15 | 3-(coumarin)-(CH$_2$)$_2$ | (2-furanyl)CH$_2$ | —N=CH—CH=CH— | base | 171.5 | 0.01 |
| 16 | 3-(coumarin)-(CH$_2$)$_2$ | 4-F—C$_6$H$_4$CH$_2$ | —N=CH—CH=CH— | H$_2$O | 167.1 | 0.04 |
| 20 | CH$_3$-C(=N-CH$_2$CH=CH$_2$)-N—(CH$_2$)$_2$ | 4-F—C$_6$H$_4$CH$_2$ | —CH=CH—CH=CH— | base | 170.5 | 0.31 |
| 6 | 3-(coumarin)-(CH$_2$)$_2$ | (4-thiazolyl)CH$_2$ | —CH=CH—CH=CH— | 2HCl 1½ H$_2$O | 187.2 | 0.16 |
| 7 | 3-(coumarin)-(CH$_2$)$_2$ | (2-pyridinyl)CH$_2$ | —N=CH—CH=CH— | 3HCl 2 H$_2$O | 190.6 | 0.04 |
| 8 | 3-(coumarin)-(CH$_2$)$_2$ | (2-thienyl)CH$_2$ | —CH=CH—CH=CH— | base | 167.6 | 0.16 |
| 9 | 3-(coumarin)-(CH$_2$)$_2$ | (2-pyridinyl)CH$_2$ | —CH=CH—CH=CH— | 2HCl 2 H$_2$O | 185.1 | 0.08 |
| 10 | 3-(coumarin)-(CH$_2$)$_2$ | (3-pyridinyl)CH$_2$ | —CH=CH—CH=CH— | H$_2$O | 147.3 | 0.31 |

°Ac = acetyl

In view of their antihistaminic properties, the compounds of formula (I) and their acid-addition salts are very useful in the treatment of allergic diseases such as, for example, allergic rhinitis, allergic conjunctivities, chronic urticaria, allergic astma and the like.

In view of their useful antihistaminic properties, the subject compounds may be formulated into various pharmaceutical forms for administration purposes. To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is also related with a method of treating allergic diseases in warm-blooded animals suffering from said allergic diseases by administering an effective anti-allergic amount of a compound of formula (I) or a pharmaceutically acceptable acid addition salt thereof.

Suitable doses administered daily to subjects are varying from 0.1 to 100 mg, more preferably from 1 to 50 mg.

The following examples are intended to illustrate and not to limit the scope of the present invention. Unless otherwise stated all parts therein are by weight.

EXAMPLES

A. PREPARATION OF INTERMEDIATES

EXAMPLE 1

A mixture of 90 parts of 4-chloro-3-nitropyridine, 71 parts of 4-fluorobenzenemethanamine, 63 parts of sodium carbonate and 900 parts of N,N-dimethylacetamide was stirred for 1 hour at 50° C. Water was added and the product was extracted with 4-methyl-2-pentanone. The extract was dried, filtered and evaporated. The residue was crystallized from acetonitrile. The product was filtered off and dried, yielding 106 parts (75%) of N-[(4-fluorophenyl)methyl]-3-nitro-4-pyridinamine; mp. 136.8° C. (intermediate 1).

In a similar manner there were also prepared:
$N^3$-[(4-fluorophenyl)methyl]-2,3-pyridinediamine as a residue (2);
N-[(4-fluorophenyl)methyl]-4-nitro-3-pyridinamine, 1-oxide (3);
2-nitro-N-(2-thienylmethyl)benzenamine (4);
N-(3-nitro)-2-pyridinyl)-2-pyridinemethanamine; mp. 113.6° C. (5); and
3-nitro-N-(2-thienylmethyl)-2-pyridinamine; mp. 100° C. (6).

EXAMPLE 2

To a stirred and cooled (0° C.) solution of 8.7 parts of N-[(4-fluorophenyl)methyl]-4-nitro-3-pyridinamine, 1-oxide and 150 parts of trichloromethane was added dropwise a solution of 10.2 parts of phosphor trichloride in 75 parts of trichloromethane. Upon completion, the mixture was allowed to reach room temperature and stirring was continued for 1 hour at reflux temperature. The reaction mixture was cooled and the solvent was evaporated. The residue was stirred in trichloromethane. The product was filtered off and dried, yielding 9 parts of N-[(4-fluorophenyl)methyl]-4-nitro-3-pyridinamine monohydrochloride (7).

EXAMPLE 3

A mixture of 11 parts of N-[(4-fluorophenyl)methyl]-4-nitro-3-pyridinamine monohydrochloride, 2 parts of a solution of thiophene in ethanol 4% and 240 parts of methanol saturated with ammonia was hydrogenated at normal pressure and at room temperature with 3 parts of platinum-on-charcoal catalyst 5%. After the calculated amount of hydrogen was taken up, the whole was warmed and the catalyst was filtered off. It was washed with 2-methoxyethanol. The filtrate was evaporated and the residue was heated in acetonitrile. After stirring and cooling, the product was filtered off and dried, yielding 6.5 parts (58%) of $N^3$[(4-fluorophenyl)methyl]-3,4-pyridinediamine monohydrochloride; mp. 208.9° C. (8).

In a similar manner there were also prepared:
$N^2$-(2-furanylmethyl)-2,3-pyridinediamine as a residue (9);
$N^4$[(4-fluorophenyl)methyl]-3,4-pyridinediamine; mp. 163.7° C. (10).
$N^1$-(2-thienylmethyl)-1,2-benzenediamine (11);
$N^2$-(2-pyridinylmethyl)-2,3-pyridinediamine; mp. 134.9° C. (12);
$N^2$-(2-thienylmethyl)-2,3-pyridinediamine; mp. 92.1° C. (13).

EXAMPLE 4

To a stirred and cooled mixture of 4 parts of sodium hydroxide in 60 parts of water were added successively 7.9 parts of carbon disulfide and 17.2 parts of ethyl 4-amino-1-piperidinecarboxylate at a temperature below 10° C. Stirring was continued for 30 minutes at this temperature. Then there were added dropwise 10.9 parts of ethyl carbonochloridate (exothermic reaction: temp. rises to about 35° C.). Upon completion, stirring was continued for 2 hours at 60° C. The reaction mixture was cooled and the product was extracted with methylbenzene. The extract was dried, filtered and evaporated, yielding 22 parts (100%) of ethyl 4-isothiocyanato-1-piperidinecarboxylate as a residue (14).

EXAMPLE 5

A mixture of 84.7 parts of ethyl 4-isothiocyanato-1-piperidinecarboxylate, 86.8 parts of $N^4$-[(4-fluorophenyl)-methyl]-3,4-pyridinediamine and 450 parts of tetrahydrofuran was stirred and refluxed for 3 hours. The reaction mixture was evaporated and the residue was crystallized from acetonitrile, yielding 90 parts (52%) of ethyl 4-[[[[4-[[(4-fluorophenyl)methyl]amino]-3-pyridinyl]-amino]thioxomethyl]amino]-1-piperidinecarboxylate; mp. 166° C. (15).

Following the same procedure and using equivalent amounts of the appropriate starting materials, there were also prepared:

ethyl 4-[[[[2-[(2-furanylmethyl)amino]phenyl]amino]-thioxomethyl]-amino]-1-piperidinecarboxylate as a residue (16);

ethyl 4-[[[3-[[(4-fluorophenyl)methyl]amino]-2-pyridinyl]amino]thioxomethylamino]-1-piperidinecarboxylate as a residue (17);

ethyl 4-[[[2-[(2-furanylmethyl)amino]-3-pyridinyl]aminothioxomethyl]amino]-1-piperidinecarboxylate; mp. 132.7° C. (18);

ethyl 4-[[[3-[[(4-fluorophenyl)methyl]amino]-4-pyridinyl]aminothioxomethyl]amino]-1-piperidinecarboxylate as a residue (19).

ethyl 4-[[[2-[(2-thienylmethyl)amino]phenyl]aminothioxomethyl]amino]-1-piperidinecarboxylate as a residue (20).

ethyl 4-[[[2-[(2-pyridinylmethyl)amino]-3-pyridinyl]aminothioxomethyl]amino]-1-piperidinecarboxylate as a residue (21).

ethyl 4-[[[2-[(2-thienylmethyl)amino]-3-pyridinyl]aminothioxomethyl]amino]-1-piperidinecarboxylate as a residue (22).

EXAMPLE 6

A mixture of 74 parts of ethyl 4-[[[2-[(2-furanylmethyl)amino]-3-pyridinyl]aminothioxomethyl]amino]-1-piperidinecarboxylate, 96 parts of mercury(II) oxide, 0.1 parts of sulfur and 800 parts of ethanol was stirred and refluxed for 3 hours. The reaction mixture was filtered over Hyflo and the filtrate was evaporated. The residue was crystallized from acetonitrile, yielding 52.5 parts (79%) of ethyl 4-[[3-(2-furanylmethyl)-3H-imidazo[4,5-b pyridin-2-yl]amino]-1-piperidinecarboxylate; mp. 149.2° C. (23).

In a similar manner there were also prepared:
ethyl 4-[[1-(2-furanylmethyl)-1H-benzimidazol-2-yl]amino]-1-piperidinecarboxylate; mp. 135.8° C. (24);

ethyl 4-[[1-[(4-fluorophenyl)methyl]-1H-imidazo[4,5-b]pyridin-2-yl]amino]-1-piperidinecarboxylate; mp. 212.5° C. (25);

ethyl 4-[[1-[(4-fluorophenyl)methyl]-1H-imidazo[4,5-c]pyridin-2-yl]amino]-1-piperidinecarboxylate dihydrochloride.monohydrate (26);

ethyl 4-[[3-[(4-fluorophenyl)methyl]-3H-imidazo[4,5-c]pyridin-2-yl]-amino]-1-piperidinecarboxylate dihydrochloride.monohydrate; mp. 168.6° C. (27);

ethyl 4-[[1-(2-thienylmethyl)-1H-benzimidazol-2-yl]amino]-1-piperidinecarboxylate; mp. 142.7° C. (28);

ethyl 4-[[3-(2-pyridinylmethyl)-3H-imidazo[4,5-b]pyridin-2-yl]amino]-1-piperidinecarboxylate; mp. 141.3° C. (29); and ethyl 4-[[3-(2-thienylmethyl)-3H-imidazo[4,5-b]pyridin-2-yl]amino]-1-piperidinecarboxylate as a residue (30).

EXAMPLE 7

A mixture of 14.5 parts of ethyl 4-(1H-benzimidazol-2-ylamino)-1-piperidinecarboxylate, 13 parts of 2-(chloromethyl)pyrazine, 10.5 parts of sodium carbonate and 135 parts of N,N-dimethylformamide was stirred and heated for 3 hours at 50° C. The whole was further stirred overnight at 70° C. The reaction mixture was cooled and poured onto water. The product was extracted with 4-methyl-2-pentanone. The extract was dried, filtered and evaporated. The residue was purified by column chromatography over silica gel using a mixture of trichloromethane and methanol (95:5 by volume) as eluent. The pure fractions were collected and the eluent was evaporated. The residue was converted into the hydrobromide salt in 2-propanone. The salt was filtered off and dried, yielding 8.7 parts (32%) of ethyl 4-[[1-(2-pyrazinylmethyl)-1H-benzimidazol-2-yl]amino]-1-piperidinecarboxylate dihydrobromide. monohydrate; mp. 178.5°–179.3° C. (31).

In a similar manner there were also prepared:
ethyl 4-[[1-(4-thiazolylmethyl)-1H-benzimidazol-2-yl]amino]-1-piperidinecarboxylate; mp. 156.2° C. (32);

ethyl 4-[[1-(3-pyridinylmethyl)-1H-benzimidazol-2-yl]amino]-1-piperidinecarboxylate; mp. 191.4° C. (33); and ethyl 4-[[1-[(2-pyridinyl)methyl]-1H-benzimidazol-2-yl]amino]-1-piperidinecarboxylate; mp. 161.5° C. (34).

EXAMPLE 8

A mixture of 50 parts of ethyl 4-[[3-(2-furanylmethyl)-3H-imidazo-[4,5-b]pyridin-2-yl]amino]-1-piperidinecarboxylate, 50 parts of potassium hydroxide, 400 parts of 2-propanol and 20 drops of water was stirred and refluxed for about 5 hours. The reaction mixture was evaporated and water was added to the residue. The product was extracted twice with 4-methyl-2-pentanone. The combined extracts were dried, filtered and evaporated. The solid residue was stirred in 1,1'-oxybisethane. The product was filtered off and dried, yielding 34 parts (85%) of 3-(2-furanylmethyl)-N-(4-piperidinyl)-3H-imidazo[4,5-b]-pyridin-2-amine; mp. 159.0° C. (35).

In the similar manner there were also prepared:
1-(2-furanylmethyl)-N-(4-piperidinyl)-1H-benzimidazol-2-amine; mp. 211.0° C. (36);

N-(4-piperidinyl)-1-(2-thienylmethyl)-1H-benzimidazol-2-amine (37); and

N-(4-piperidinyl)-3-(2-thienylmethyl)-3H-imidazo[4,5-b]pyridin-2-amine; mp. 189.6°–193.5° C. (38).

EXAMPLE 9

A mixture of 23.8 parts of ethyl 4-[[3-[(4-fluorophenyl)methyl]-3H-imidazo[4,5-c]pyridin-2-yl]amino]-1-piperidine carboxylate and 275 parts of a hydrobromic acid solution 48% in water was stirred overnight at 80° C. The reaction mixture was evaporated and the residue was crystallized from ethanol, yielding 14.7 parts (48%) of 3-[(4-fluorophenyl)methyl]-N-(4-piperidinyl)-3H-imidazo[4,5-c]pyridin-2-amine dihydrobromide monohydrate; mp. 291.6° C. (39).

In a similar manner there were also prepared:
1-[(4-fluorophenyl)methyl]-N-(4-piperidinyl)-1H-imidazo[4,5-b]pyridin-2-amine dihydrobromide; mp. +300.6° C. (40);

1-[(4-fluorophenyl)methyl]-N-(4-piperidinyl)-1H-imidazo[4,5-c]-pyridin-2-amine dihydrobromide; mp. 279.4° C. (41);

N-(4-piperidinyl)-1-(4-thiazolylmethyl)-1H-benzimidazol-2-amine dihydrobromide monohydrate; mp. 223.5° C. (42);

N-(4-piperidinyl)-1-(2-pyrazinylmethyl)-1H-benzimidazol-2-amine trihydrobromide; (43);

N-(4-piperidinyl)-1-(3-pyridinylmethyl)-1H-benzimidazol-2-amine trihydrobromide; mp. >260° C. (44);

N-(4-piperidinyl)-3-(2-pyridinylmethyl)-3H-imidazo[4,5-b]pyridin-2-amine trihydrobromide; mp. 265.5° C. (45); and
N-(4-piperidinyl)-1-[(2-pyridinyl)methyl]-1H-benzimidazol-2-amine trihydrobromide; mp. 295.9° C. (46).

EXAMPLE 10

A mixture of 8.62 parts of 2-chloroacetonitrile, 37 parts of (cis+trans)-1-[(4-fluorophenyl)methyl]-N-(3-methyl-4-piperidinyl)-1H-benzimidazol-2-amine, 15.9 parts of sodium carbonate and 270 parts of N,N-dimethylformamide was stirred for 2 hours at 40° C. The reaction mixture was poured onto water. The product was extracted twice with 4-methyl-2-pentanone. The combined organic layers were dried, filtered and evaporated. The residue was crystallized from 1,1'-oxybisethane. The product was filtered off and dried, yielding 25.1 parts (57%) of (cis+trans)-4-[[1-[(4-fluorophenyl)methyl]-1H-benzimidazol-2-yl]amino]-3-methyl-1-piperidineacetonitrile; mp. 150.1° C. (47).

In a similar manner there were also prepared:
4-[[1-[(2-furanyl)methyl]-1H-benzimidazol-2-yl]amino]-1-piperidine-acetonitrile; mp. 194.4° C. (48); and
4-[[3-[(4-fluorophenyl)methyl]-3H-imidazo[4,5-b]pyridin-2-yl]-amino]-1-piperidineacetonitrile; mp. 183.7° C. (49).

EXAMPLE 11

A mixture of 15 parts of 4-[[3-[(4-fluorophenyl)methyl]-3H-imidazo [4,5-b]pyridin-2-yl]amino]-1-piperidineacetonitrile and 400 15 parts of methanol saturated with ammonia was hydrogenated at normal pressure and at room temperature with 3 parts of Raney-nickel catalyst. After the calculated amount of hydrogen was taken up, the catalyst was filtered off and the filtrate was evaporated. The residue was crystallized from a mixture of acetonitrile and 2,2'-oxybis-propane, yielding 10 parts (68%) of N-[1-(2-aminoethyl)-4-piperidinyl]-3-[(4-fluorophenyl)methyl]-3H-imidazo[4,5-b]pyridin-2-amine; mp. 174.5° C. (50). In a similar manner there were also prepared:
N-[1-(2-aminoethyl)-4-piperidinyl]-1-(2-furanylmethyl)-1H-benzimidazol -2-amine; mp. 163.0° C. (51);
(cis+trans)-N-[1-(2-aminoethyl)-3-methyl-4-piperidinyl]-1-[(4-fluorophenyl) methyl]-1H-benzimidazol-2-amine; mp. 132.2° C. (52).

EXAMPLE 12

A mixture of 9 parts of oxirane, 3.24 parts of 1-(4-fluorophenyl-methyl) -N-(4-piperidinyl)-H-benzimidazol-2-amine and 400 parts of methanol was stirred first overnight at room temperature and further for 4 hours at 50° C. The reaction mixture was evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from a mixture of 4-methyl-2-pentanone and 2,2'-oxybispropane, yielding 15 parts of 4-[1-(4-fluorophenylmethyl)-1H-benzimidazol-2-ylamino]-1-piperidineethanol; mp. 138.7° C. (53).

EXAMPLE 13

To 2 parts of a solution of 2 parts of thiophene in 40 parts of ethanol were added 15 parts of ethyl 4-oxo-1-piperidinecarboxylate, 25 parts kof 1-(4-fluorophenylmethyl)-N-(4-piperidinyl)-1H-benzimidazol-2-amine, and 200 parts of methanol. The whole was hydrogenated at normal pressure and at room temperature with 5 parts of platinum-on-charcoal catalyst 5%. After the calculated amount of hydrogen was taken up, the catalyst was filtered off and the filtrate was evaporated. The residue was purified by column chromatography over silica gel using a mixture of trichloromethane and methanol (90:10 by volume) as eluent. The pure fractions were collected and the eluent was evaporated. The residue was converted into the hydrochloride salt in 2-propanol and 2-propanone. The salt was filtered off and dried, yielding 13.6 parts of ethyl 4-[1-(4-fluorophenylmethyl)-1H-benzimidazol-2-ylamino][1,4'-bipiperidine]-1'-carboxylate dihydrochloride monohydrate; mp. 260° C. (54).

Following the same procedure and using equivalent amounts of the appropriate starting materials, there was also prepared:
1-[(4-fluorophenyl)methyl]-N-[1-(phenylmethyl)-[1,3'-bipiperidin]-4-yl]-1H-benzimidazol-2-amine; mp. 174.6° C. (55).

EXAMPLE 14

A mixture of 21 parts of ethyl 4-[1-(4-fluorophenylmethyl)-1H-benzimidazol-2-ylamino][1,4'-bipiperidine]-1'-carboxylate and 450 parts of hydrobromic acid solution 48% was stirred and refluxed for 16 hours. The reaction mixture was evaporated. From the residue the free base was liberated in the conventional manner with sodium hydroxide in water and extracted with dichloromethane. The extract was dried, filtered and evaporated, yielding 8 parts (50%) of N-[1-(4-fluorophenylmethyl) -1H-benzimidazol-2yl]-[1,4'-bipiperidine]-4-amine as a residue (56).

EXAMPLE 15

A mixture of 11.3 parts of 1-[(4-fluorophenyl)methyl]-N-[1'-(phenylmethyl) -[1,3'-bipiperidin]-4-yl]-1H-benzimidazol-2-amine and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was suspended in 2,2'-oxybispropane. The product was filtered off and dried, yielding 8.5 parts (91.5%) of N-([1,3'-bipiteridin]-4-yl)-1-[(4-fluorophenylmethyl]-1H-benzimidazol-2-amine (57).

EXAMPLE 16

To a stirred and hot (50° C.) mixture of 4.1 parts of 2H-3,1-benzoxazine-2,4(1H)-dione and 31.5 parts of N,N-dimethylformamide was added dropwise a solution of 9.4 parts of N-[1-(2-aminoethyl)-4-piperidinyl]-1-[(4-fluorophenyl)methyl]-1H-benzimidazol-2-amine in 31.5 parts of N,N-dimethylformamide at 50° C. Upon completion, stirring was continued for 3 hours at 50° C. Water was added and the product was extracted with 4-methyl-2- pentanone. The extract was dried, filtered and evaporated. The residue was crystallized from acetonitrile, yielding 9.8 parts (80%) of 2-amino-N-[2-[4-[1-(4-fluorophenyl)-methyl]-1H-benzimidazol-2-yl]amino]-1-piperidinyl]ethyl]benzamide; mp. 171.7° C. (58).

In a similar manner there was also prepared:
2-(ethylamino)-N-[2-[4-[[1-[4-(fluorophenyl)methyl]-H-benzimidazol-2-yl]amino]-1-piperidinyl]ehtyl]benzenamide monohydrate; mp. 139.8° C. (59).

EXAMPLE 17

To a stirred solution of 3 parts of 3-(2-hydroxyethyl)-2,4(1H,3H)-pyrimidinedione and 45 parts of trichloromethane were added dropwise 8 parts of thionyl chloride. Upon completion, stirring was continued for 1 hour at reflux temperature. The reaction mixture was cooled. The precipitated product was filtered off and crystallized from 2-propanol, yielding 3.1 parts of 3-(2-chloroethyl)-2,4(1H,3H)-pyrimidinedione; mp. 170° C. (60).

B. PREPARATION OF FINAL COMPOUNDS

EXAMPLE 18

A mixture of 1.6 parts of 1-chloro-2-(ethenyloxy)ethane, 7.3 parts of 1-(4-fluorophenylmethyl)-N-(4-piperidinyl)-1H-benzimidazol-2-amine dihydrobromide, 3.1 parts of sodium carbonate, 0.1 parts of potassium iodide and 135 parts of N,N-dimethylformamide was stirred and heated overnight at 70° C. The reaction mixture was poured onto water and the product was extracted with 4-methyl-2-pentanone. The extract was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from acetonitrile, yielding 1.9 parts (32%) of N-[1-[2-(ethenyloxy)ethyl]-4-piperidinyl]-1-(4-fluorophenylmethyl)-1H-benzimidazol-2-amine; mp. 138.5° C. (compound 1).

In a similar manner there were also prepared:

1-[(4-fluorophenyl)methyl]-N-[1-[2-(4-methoxyphenyl)ethyl]-4-piperidinyl]-1H-imidazo[4,5-b]pyridin-2-amine; mp. 186.8° C. (compound 2);

1-[(4-fluorophenyl)methyl]-N-[1-[2-(4-methoxyphenyl)ethyl]-4-piperidinyl]-1H-imidazo[4,5-c]pyridin-2-amine; mp. 184.5° C. (compound 3);

3-[(4-fluorophenyl)methyl]-N-[1-[2-(4-methoxyphenyl)ethyl]-4-piperidinyl]-3H-imidazo[4,5-c]pyridin-2-amine (E)-2-butenedioate (1:2); mp. 202.8° C. (compound 4);

3-[2-[4-[[1-[(4-fluorophenyl)methyl]-1H-benzimidazol-2-yl]amino]-1-piperidinyl]ethyl]-2,4-(1H,3H)-pyrimidinedione; mp. 245.8° C. (compound 5);

3-[2-[4-[[1-(4-thiazolylmethyl)-1H-benzimidazol-2-yl]amino]-1-piperidinyl]ethyl]-2H-1-benzopyran-2-one dihydrochloride.sesquihydrate; mp. 187.2° C.(compound 6);

3-[2-[4-[[3-(2-pyridinylmethyl)-3H-imidazo[4,5-b]pyridin-2-yl]amino]-1-piperidinyl]ethyl]-2H-1benzopyran-2-one trihydrochloride.dihydrate mp. 190.6° C. (compound 7);

3-[2-[4-[[1-(2-thienylmethyl)-1H-benzimidazol-2-yl]amino]-1-piperidinyl]ethyl]-2H-1-benzopyran-2-one; mp. 167.6° C. (compound 8);

3-[2-[4-[[1-(2-pyridinylmethyl)-1H-benzimidazol-2-yl]amino]-1-piperidinyl]ethyl]-2H-1-benzopyran-2-one dihydrochloride.dihydrate; mp. 185.1° C. (compound 9);

3-[2-[4-[[1-(3-pyridinylmethyl)-1H-benzimidazol-2-yl]amino]-1-piperidinyl]ethyl]-2H-1-benzopyran-2-one monohydrate; mp. 147.3° C. (compound 10);

3-[2-[4-[[1-(2-thienylmethyl)-1H-benzimidazol-2-yl]amino]-1-piperidinyl]ethyl]-2H-1-benzopyran-2-one; mp. 164.6° C. (compound 11)

EXAMPLE 19

A mixture of 3.8 parts of 3-(2-bromomethyl)-2H-1-benzopyran-2-one, 7.3 parts of 1-[(4-fluorophenyl)methyl]-N-(4-piperidinyl)-1H-benzimidazol-2-amine dihydrobromide, 4.8 parts of sodium carbonate and 135 parts of N,N-dimethylformamide was stirred and heated overnight at 70° C. The reaction mixture was poured onto water. The product was extracted with trichloromethane. The extract was dried, filtered and evaporated. The residue was purified by column-chromatography over silica gel using a mixture of trichloromethane and methanol, saturated with ammonia, (96:4 by volume) as eluent. The pure fractions were collected and the eluent was evaporated. The residue was crystallized from acetonitrile, yielding 1.6 parts (21.5%) of 3-[2-[4-[[1-[(4-fluorophenyl)methyl]-1H-benzimidazol-2-yl]amino]-1-piperidinyl]ethyl]-2H-1-benzopyran-2-one; mp. 168.4° C. (compound 12).

In a similar manner there were also prepared:

N-[1-[2:(4-methoxyphenyl)ethyl]-4-piperidinyl]-1-[(2-pyrazinyl)methyl]-1H-benzimidazol-2-amine; mp. 127.4° (compound 13);

3-[2-[4-[[1-(2-furanylmethyl)-1H-benzimidazol-2-yl]amino]-1-piperidinyl]ethyl]-2H-1-benzopyran-2-one monohydrate; mp. 133.2° C. (compound 14);

3-[2-[4-[[3-(2-furanylmethyl)-3H-imidazo[4,5-b]pyridin-2-yl]amino]-1-piperidinyl]ethyl]-2H-1-benzopyran-2-one; mp. 171.5° C.(compound 15); and 3-[2-[4-[[3-[(4-fluorophenyl)methyl]-3H-imidazo [4,5-b]pyridin-2-yl]-amino]-1- piperidinyl]ethyl]-2H-1-benzopyran-2-one monohydrate; mp. 167.1° C. (compound 16).

EXAMPLE 20

A mixture of 4.7 parts of 1-(2-chloroethyl)-4-methoxybenzene, 14 parts of N-(4-piperidinyl)-1-(4-thiazolylmethyl)-1H-benzimidazol-2-amine dihydrobromide.monohydrate, 15 parts of sodium carbonate, 0.3 parts of sodium iodide and 90 parts of N,N-dimethylacetamide was stirred overnight at 80° C. Water was added and the product was extracted with 4-methyl-2-pentanone. The extract was dried, filtered and evaporated. The oily residue was converted into the hydrobromide salt in ethanol. The salt was filtered off and dried, yielding 9 parts of N-[1-[2-(4-methoxyphenyl)ethyl]-4-piperidinyl]-1-(4-thiazolyl)-methyl)-1H-benzimidazol-2-amine dihydrobromide. dihydrate; mp. 239.2° C. (compound 17).

EXAMPLE 21

To a stirred mixture of 4 parts of N-[1-(4-fluorophenylmethyl)-1H-benzimidazol-2-yl]-[1,4'-bipiperidine]-4-amine, 1 part ofN,N-diethylethanamine and 91 parts of dichloromethane was added dropwise a solution of 1.6 parts of 4-fluorobenzoyl chloride in 39 parts of dichloromethane: slightly exothermic reaction, the temperature rises from 25° C. to 30° C. Upon completion, stirring was continued for one hour at room temperature. The reaction mixture was purified by high performance liquid chromatography using a mixture of trichloromethane, hexane and methanol (45:45:10 by volume) as eluent. The pure fractions were collected and the eluent was evaporated, yielding 1.8 parts (34%) of 1'-(4-fluorobenzoyl-N-[1-(4-fluorophenylmethyl)-1H-benzimidazol-2-yl]-[1,4'-bipiperidine]-4-amine; mp. 194.3° C.; (compound 18).

Following the same procedure and using equivalent amounts of the appropriate starting materials, there was also prepared:
N,N-diethyl-4-[1-(4-fluorophenylmethyl)-1H-benzimidazol-2-ylamino]-[1,4'-bipiperidine]-1'-carboxamide; mp. 176.6° C. (compound 19).

EXAMPLE 22

A mixture of 1.64 parts of 2-methyl-1H-imidazole, 9.2 parts of N-[1-(2-chloroethyl)-4-piperidinyl]-1-(4-fluorophenylmethyl)-1H-benzimidazol-2-amine dihydrochloride, 6.4 parts of sodium carbonate and 135 parts of N,N-dimethylformamide was stirred overnight at 60° C. The reaction mixture was poured into water. The product was extracted with trichloromethane. The extract was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from acetonitrile. The product was filtered off and dried, yielding 2.6 parts (30% of 1-[(4-fluorophenyl)methyl]-N-[1-[2-(2-methyl-1H-imidazol-1-yl)ethyl]-4-piperidinyl]-1H-benzimidazol-2-amine; mp. 170.5° C. (compound 20).

EXAMPLE 23

A mixture of 1.9 parts of dimethyl cyanocarbonimidodithioate, 4.8 parts of N-[1-(2-aminoethyl)-4-piperidinyl]-3-[(4-fluorophenyl)-methyl]-3H-imidazo[4,5-b]pyridin-2-amine and 80 parts of methanol was stirred for 2 hours at room temperature. The reaction mixture was evaporated and the residue was crystallized from acetonitrile, yielding 4.5 parts (74%) of S-methyl N'-cyano-N-[2-[4-[[3-[(4-fluorophenyl)methyl]-3H-imidazo[4,5-b]pyridin-2-yl]amino]-1-piperidinyl]ethyl]carbamimidothioate; mp. 172.2° C. (compound 21).

In a similar manner there was also prepared:
S-methyl N'-cyano-N-[2[4-[[1-[[(4-fluorophenyl)methyl]-1H-benzimidazol-2-yl]amino]-1-piperidinyl]ethyl]carbamimidothioate (compound 22).

EXAMPLE 24

A mixture of 1.5 parts of N-methyl-N'-nitro-N-nitrosoquanidine, 3.7 parts of N-[1-(2-aminoethyl)-4-piperidinyl]-1-(4-fluorophenylmethyl)-1H-benzimidazol-2-amine and 80 parts of ethanol 50% was stirred overnight at room temperature. The reaction mixture was evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from 2-propanol. The product was filtered off and dried overnight at 110° C., yielding 1.5 parts (33%) of N-[2-[4-[[1-[(4-fluorophenyl)methyl]-1H-benzimidazol-2-yl]amino]-1-piperidinyl]ethyl]-N'-nitroguanidine; mp. 146.7° C. (compound 23).

EXAMPLE 25

A mixture of 1.6 parts of 2,2;1 diethoxyethanamine, 4.6 parts of S-methyl N'-cyano-N-[2-[4-[[1-[(4-fluorophenyl)methyl]-1H-benzimidazol-2-yl]-1-piperidinyl]ethyl]carbamimidothioate and 40 parts of 1-butanol was stirred and refluxed overnight. The reaction mixture was evaporated. The residue was purified by column chromatography over silica gel using a mixture of trichloromethane and methanol (93:7 by volume) as eluent. The pure fractions were collected and the eluent was evaporated. The residue was converted into the (E)-2-butenedioate salt in ethanol. The salt was filtered off and dried, yielding 2 parts of N''-cyano-N-(2,2-dimethoxyethyl)-N'-[2-[4-[[1-[(4-fluorophenyl)methyl]-1H-benzimidazol-2-yl]amino]-1-piperidinyl]ethyl]guanidine (E)-2-butenedioate(1:2) (compound 24).

Following the same procedure and using equivalent amounts of the appropriate starting materials, there were also prepared:
N'''-cyano-N-[2-[4-[[1-[(4-fluorophenyl)methyl]-1H-benzimidazol-2-yl]-amino]-1-piperidinyl]ethyl-N',N'-dimethylguanidine; mp. 110.5° C. (compound 25).
N'''-cyano-N-[2-[4-[[1-[(4-fluorophenyl)methyl]-1H-benzimidazol-2-yl]-aminol]-1-piperidinyl]ethyl]-N'-[2-(4-morpholinyl)ethyl]guanidine monohydrate; mp. 125.6° C. (compound 26).

EXAMPLE 26

A solution of 5.71 parts of (cis+trans)-N-[1-(2-aminoethyl)-3-methyl-4-piperidinyl]-1-[(4-fluorophenyl)methyl]-1H-benzimidazol-2-amine, 2.84 parts of 1,1'-thiocarbonylbis[1H-imidazole] in 180 parts of tetrahydrofuran was stirred for 2 hours at room temperature, 0.9 Parts of gazeous N-methylmethanamine was bubbled, during 30 minutes, through the mixture. Stirring was continued overnight at room temperature. The whole was evaporated. The residue was purified by column chromatography over silica gel using a mixture of trichloromethane and methanol (from 100:0 to 90:10 by volume) as eluent. The pure fractions were collected and the eluent was evaporated. The residue was stirred in 2,2'-oxybispropane. The product was filtered off and dried, yielding 2.3 parts (32.7%) of cis-N-[2-[4-[[1-[(4-fluorophenyl)methyl]-1H-benzimidazol-2-yl]amino]-3-methyl-1-piperidinyl]ethyl]-N',N'-dimethylthiourea; mp. 126.7° C. (compound 27).

In a similar manner there was also prepared:
N-[2-[4-[[1-[(4-fluorophenyl)methyl]-1H-benzimidazol-2-yl]amino]-1-piperidinyl]ethyl]-4-morpholinecarbothioamide; mp. 191.6° C. (compound 28).

EXAMPLE 27

A mixture of 0.9 parts of piperidine, 4.1 parts of 1-(4-fluorophenylmethyl)-N-[1-(2-isothiocyanatoethyl)-4-piperidinyl]-1H-benzimidazol-2-amine and 135 parts of tetrahydrofuran was stirred for 2 hours at room temperature. The reaction mixture was evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from acetonitrile, yielding 1 part (20.2%) of N-[2-[4-[[1-[(4-fluorophenyl)methyl]-1H-benzimidazol-2-yl]amino]-1-piperidinyl]ethyl]-1-piperidinecarbothioamide; mp. 175.6° C. (compound 29).

EXAMPLE 28

A mixture of 3.75 parts of 3-amino-1-propanol, 20.5 parts of 1-(4-fluorophenylmethyl)-N-[1-(2-isothiocyanatoethyl)-4-piperidinyl]-1H-benzimidazol-2-amine and 450 parts of tetrahydrofuran was stirred for 3 hours at room temperature. The reaction mixture was evaporated. The residue was purified by column chromatography over silica gel using a mixture of trichloromethane and methanol (96:4 by volume) as eluent. The pure fractions were collected and the eluent was evaporated. The residue was crystallized from acetonitrile, yielding 16 parts (64%) of N-[2-[4-[[1-[(4-fluorophenyl)methyl]-1H-benzimidazol-2-yl]amino]-1-piperidinyl]ethyl]-N'(3-hydroxypropyl)thiourea monohydrate; mp. 124.6° C. (compound 30).

Following the same procedure and using equivalent amounts of the appropriate starting materials, there were also prepared:

N-[2-[4-[[1-(4-fluorophenyl)methyl]-1H-benzimidazol-2-yl]amino]-1-piperidinyl]ethyl]-N',N'-dimethylthiourea; mp. 159.7° C. (compound 31).

N,N-diethyl-N'-[2-[4-[[1-[(4-fluorophenyl)methyl]-1H-benzimidazol-2-yl]-amino]-1-piperidinyl]ethyl]thiourea; mp. 175.5° C. (compound 32).

N-[2-[4-[[1-[(4-fluorophenyl)methyl]-1H-benzimidazol-2-yl]amino]-1-piperidinyl]ethyl]-N'(2-phenylethyl)-thiourea (E)-2-butenedioate(1:2); mp. 196.8° C. (compound 33).

N-[2-[4-[[1-[(4-fluorophenyl)methyl]-1H-benzimidazol-2-yl]amino]-1-piperidinyl]ethyl]hydrazinecarbothioamide monohydrate; mp. 183.8° C. (compound 34).

EXAMPLE 29

A mixture of 1.3 parts of 2-chloro-3-pyridinamine, 4.1 parts of 1-(4-fluorophenylmethyl)-N-[1-(2-isothiocyanatoethyl)-4-piperidinyl]-1H-benzimidazol-2-amine and 80 parts of ethanol was stirred and refluxed overnight. The reaction mixture was evaporated. Water and ammonia were added to the residue and the product was extracted with trichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from acetonitrile. The product was filtered off and dried, yielding 1.4 parts of ethyl [2-[4-[[1-[(4-fluorophenyl)-methyl]-1H-benzimidazol-2-yl]amino]-1-piperidinyl]ethyl]carbamothioate; mp. 148.6° C. (compound 35).

EXAMPLE 30

A mixture of 0.55 part of isocyanatomethane, 4 parts of N-[1-(4-fluoropenylmethyl)-1H-benzimidazol-2-yl]-[1,4'-bipiperidine]-4-amine, 80 parts of ethanol and 65 parts of dichloromethane was stirred for 3 hours at room temperature. The reaction mixture was evaporated. The residue was purified by HPLC over silica gel using a mixture of trichloromethane, hexane and methanol, saturated with ammonia, (45:45:10 by volume) as eluent. The pure fractions were collected and the eluent was evaporated. The residue was crystallized from acetonitrile, yielding 1 part (25%) of 4-[[1-(4-fluorophenyl)methyl]-1H-benzimidazol-2-ylamino]-N-methyl-[1,4'-bipiperidine]-1'-carboxamide monohydrate; mp. 152.4° C. (compound 36).

EXAMPLE 31

A mixture of 0.8 parts of isothiocyanatomethane, 4 parts of N-([1,3'-bipiperidin]-4-yl)-1-[(4-fluorophenyl)methyl[-1H-benzimidazol-2 -amine and 90 parts of tetrahydrofuran was stirred overnight at room temperature. The reaction mixture was evaporated. The residue was purified by column chromatography over silica gel using a mixture of trichloromethane and methanol, saturated with ammonia, (96:4 by volume) as eluent. The pure fractions were collected and the eluent was evaporated. The residue was crystallized from acetonitrile, yielding 3.7 parts (77%) of 4-[[1-[(4-fluorophenyl)methyl]-1H-benzimidazol-2-yl]amino]-N-methyl-[1,3'-bipiperidine]-1'-carbothioamide; mp. 218.8° C. (compound 37).

In a similar manner there were also prepared:

4-[[1-[(4-fluorophenyl)methyl]-1H-benzimidazol-2-yl]amino]-N-methyl-[1,4'-bipiperidine]-1'-carboxamide; mp. 222.7° C. (compound 38).

N-cyclohexyl-N'-[2-[4-[[1-[(4-fluorophenyl)methyl]-1H-benzimidazol-2-yl]amino]-1-piperidinyl]ethyl]thiourea; mp. 177° C. (compound 39).

N-[2-[4-[[1-[(4-fluorophenyl)methyl]-1H-benzimidazol-2-yl]amino]-1-piperidinyl]ethyl]-N'phenylthiourea; mp. 162.7° C. (compound 40).

N-[2-[4-[1-(4-fluorophenylmethyl)-1H-benzimidazol-2-ylamino]-1-piperidinyl]ethyl]-N'(4-methoxyphenyl)-thiourea; mp. 165.9° C. (compound 41).

EXAMPLE 32

To a stirred mixture of 1.9 parts of 2-oxo-2H-benzopyran-3-carboxylic acid, 4.04 parts of N,N-diethylethanamine and 195 parts of dichloromethane were added 2.55 parts of 2-chloro-1-methylpyridinium iodide and stirring was continued for 30 minutes at room temperature. Then there was added a solution of 3.68 parts of 4-[1-(4-fluorophenyl-methyl)-1H-benzimidazol-2-ylamino]-1-piperidineethanol in 130 parts of dichloromethane and the whole was stirred for 1 hour at room temperature. The reaction mixture was washed with water. The organic phase was dried, filtered and evaporated. The residue was purified by column chromatography over silica gel using a mixture of trichloromethane and methanol, saturated with ammonia, (96:4 by volume) as eluent. The pure fractions were collected and the eluent was evaporated. The residue was converted into the (E)-2-butenedioate salt in methanol. The salt was filtered off and dried, yielding 0.3 parts (4%) of [2-[4-[[1-[(4-fluorophenyl)methyl]-1H-benzimidazol-2-yl]amino]-1-piperidinyl]ethyl]-2-oxo-2H-benzopyran-3-carboxylate (E)-2-butenedioate(1:2); mp. 205.0° C. (compound 42).

Following the same procedure and using equivalent amounts of the appropriate starting materials, there was also prepared;

N-[2-[4-[[1-[(4-fluorophenyl)methyl]-1H-benzimidazol-2-yl]amino]-1-piperidinyl]ethyl]4-oxo-4H-1-benzopyran-2-carboxamide (E)-2-butenedioate(1:2); mp. 248.7° C. (compound 43).

EXAMPLE 33

To a stirred and cooled (below 10° C.) mixture of 3.8 parts of 2-oxo-2H-1-benzopyran-3-carboxylic acid, 2.2 parts of N,N-diethylethanamine and 225 parts of trichloromethane was added dropwise a solution of 1.9 parts of methyl carbonochloridate in 75 parts of trichloromethane. Upon completion, stirring was continued for 30 minutes at room temperature. This solution was added dropwise to a stirred and cooled solution of 6.6 parts of N-[1-(2-aminoethyl)-4-piperidinyl]-1-[(4-fluorophenyl)methyl]-1H-benzimidazol-2-amine in 75 parts of trichloromethane at 5° C. The whole was stirred for 1 hour while the mixture was allowed to reach room temperature. The reaction mixture was washed successively with water, a sodium hydroxide solution 10% and again with water. The organic phase was dried, filtered and evaporated. The residue was purified by column chromatography over silica gel using a mixture of trichloromethane and methanol (95:5 by volume) as eluent. The pure fractions were collected and the eluent was evaporated. The residue was converted into the (E)-2-butenedioate salt in methanol. The salt was filtered off and dried, yielding 6.6 parts (47.5%) of N-[2-[4-[[1-[(4-fluorophenyl)-methyl]-1H-benzimidazol-2-yl]amino]-1-piperidinyl]ethyl]-2-oxo-2H-1-benzopyran-3-carboxamide (E)-2-butenedioate(1:2); mp. 216.8° C. (compound 44).

EXAMPLE 34

A mixture of 4.4 parts of N-(5-bromo-1,3,4-thiadiazol-2-yl)-acetamide, 7.3 parts of N-[1-(2-aminoethyl)-4-piperidinyl]-1-[(4-fluorophenyl)methyl]-1H-benzimidazol-2-amine, 3.18 parts of sodium carbonate and 135 parts of N,N-dimethylformamide was stirred overnight at 80°–90° C. The reaction mixture was evaporated. The residue was purified by column chromatography over silica gel using a mixture of trichloromethane and methanol (90:10 by volume) as eluent. The pure fractions were collected and the eluent was evaporated. The residue was crystallized from a mixture of acetonitrile and 2,2'-oxybispropane, yielding 1.7 parts of N-[2-[4-[[1-[(4-fluorophenyl)methyl]-1H-benzimidazol-2-yl]amino]-1-piperidinyl]ethyl]formamide; mp. 153.2° C. (compound 45).

EXAMPLE 35

A mixture of 5.09 parts of N-[1-(2-aminoethyl)-4-piperidinyl]-1-(2-furanylmethyl)-1H-benzimidazol-2-amine and 54 parts of N,N-dimethylformamide was stirred and heated at 50° C. and there was added dropwise a solution of 2.8 parts of dihydro-3-phenyl-2H-pyran-2,6(3H)dione in 18 parts of N,N-dimethylformamide. Upon completion, stirring was continued overnight at 50° C. The residue was purified by column chromatography over silica gel using a mixture of trichloromethane and methanol, saturated with ammonia, (95:5 by volume) as eluent. The pure fractions were collected and the eluent was evaporated. The residue was from a mixture of acetonitrile and 2,2'-oxybispropane, yielding 1.8 parts of N-[2-[4-[[1-(2-furanylmethyl)-1H-benzimidazol-2-yl]amino]-1-piperidinyl]ethyl]formamide hemihydrate; mp. 125.2° C. (compound 46).

EXAMPLE 36

A mixture of 30 parts of 2-furanmethanol, 300 parts of a formaldehyde solution 4% in water and 145 parts of 1-[(4-fluorophenyl)-methyl]-N-(4-piperidinyl)-1H-benzimidazol-2-amine dihydrobromide was stirred at 3° C. The mixture was allowed to reach slowly room temperature and stirring was continued for 3 days at room temperature. The reaction mixture was alkalized and extracted with dichloromethane. The extract was dried, filtered and evaporated. The residue was purified by column chromatography over silica gel using first trichloromethane and then a mixture of trichloromethane and methanol (90:10 by volume) as eluent. The pure fractions were collected and the eluent was evaporated. The residue was converted into the (E)-2-butenedioate salt and the free base was liberated again in the conventional manner. It was crystallized from a mixture of 2-propanone and 2,2'-oxybispropane, yielding 57 parts (44%) of 5-[[4-[[1-[(4-fluorophenyl)methyl]-1H-benzimidazol-2-yl]amino]-1-piperidinyl]methyl]-2-furanmethanol; mp. 148.8° C. (compound 47).

EXAMPLE 37

To a stirred solution of 6.5 parts of 5-[[4-[[1-](4-fluorophenyl)-methyl]-1H-benzimidazol-2yl]amino]-1-piperidinyl]methyl]-2-furanmethanol in 180 parts of N,N-dimethylformamide was added portionwise 1 part of a sodium hydride dispersion 50.% at room temperature. After stirring for 1 hour, a solution of 1.6 parts of 2-chloropyrimidine in N,N-dimethylformamide was added dropwise. Upon completion, stirring was continued overnight at room temperature. The reaction mixture was poured into water and the product was extracted with dichloromethane. The extract was dried, filtered and evaporated. The residue was purified by column chromatography over silica gel using first trichloromethane and then a mixture of trichloromethane and methanol (95.5 by volume) as eluent. The first fraction was collected and the eluent was evaporated. The residue was crystallized from a mixture of 4-methyl-2-pentanone and 2,2'-oxybispropane, yielding 2.1 parts of 1-[(4-fluorophneyl)methyl]-N-[1-[[5-[(2-pyrimidinyloxy)methyl]-2-furanyl]methyl]-4-piperidinyl]-1H-benzimidazol-2-amine; mp. 167.8° C. (compound 48).

EXAMPLE 38

To a stirred solution (0° C.) of 11.4 parts of 2-aminoethanethiol hydrochloride in 48 parts of concentrate hydrochloride acid were added portionwise 25 parts of 5-[[4-[[1-[(4-fluorophenyl)methyl]-1H-benzimidazol-2-yl]amino]-1-piperidinyl]methyl]-2-furanmethanol. Upon completion, stirring was continued first overnight at 0° C. and then for 4 days at room temperature. The reaction mixture was alkalized with a dilute potassium hydroxide solution and the product was extracted with dichloromethane. The extract was dried, filtered and evaporated. The residue was purified by filtration over silica gel using a mixture of trichloromethane and methanol, saturated with ammonia, (90:10 by volume) as eluent. The pure fractions were collected and the eluent was evaporated, yielding 24 parts (88.5%) of N-[1-[[5-[)2-aminoethyl)-thiomethyl]-2-furanlyl]methyl]-4-piperidinyl]-1-[(4-fluorophenyl)methyl]-1H-benzimidazol-2-amine as an oily residue (49).

A mixture of 1.14 parts of 2-chloropyrimidine, 5 parts of N-[1-[[5-[(2-aminoethyl)thiomethyl]-2-furanyl]methyl]-4-piperidinyl]-1-[(4-fluorophenyl)methyl]-1H-benzimidazol-2-amine, 8 parts of sodium hydrogen carbonate and 80 parts of ethanol was stirred and refluxed overnight. The reaction mixture was filtered and the filtrate was evaporated. The residue was purified by column chromatography over silica gel using a mixture of trichloromethane and methanol (97:3 by volume) as eluent. The main fraction was collected and the eluent was evaporated. The residue was crystallized from 1,1'-oxybisethane, yielding 1.2 parts (21%) of 1-[(4-fluorophenyl)methyl]-N-[1-[[5-]]2-(2-pyrimidinylamino)ethyl]thiomethyl]-2-furanyl]methyl]-4-piperidinyl]-1H-benzimidazol-2-amine; mp. 128.9° C. (compound 50).

EXAMPLE 39

A mixture of 7.7 parts of 2-amino-N-[2-[4-[[1-[(4-fluorophenyl)-methyl]-1H-benzimidazol-2-yl]amino]-1-piperidinyl]ethyl]benzamide, 20 parts of acetic acid anhydride and 80 parts of water was stirred for 4 hours at 100° C. Water was added and the whole was alkalized with ammonium hydroxide. The product was extracted with trichloromethane. The extract was dried, filtered and evaporated. The residue was crystallized from 4-methyl-2-pentanone. The product was filtered off and recrystallized from acetonitrile, yielding 7.7 parts of 2-(acetylamino)-N-[2-[4-[[1-[(4-fluorophenyl)methyl]-1H-benzimidazol-2-yl]amino]-1-piperidinyl]ethyl]benzamide; mp. 170.9° C. (compound 51).

In a similar manner there was also prepared:
2-(acetylethylamino(1)-N-[2-[4-[[(1-[(4-fluorophenyl)methyl]-1H-benzimidazol-2yl]amino]-1-piperidinyl]ethyl]benzamide (E) -2-butenedioate(1:2); mp. 175.2° C. (compound 52).

EXAMPLE 40

To a stirred mixture of 4.4 parts of N-[1-[2-(4-aminophenyl)ethyl]-4-piperidinyl]-1-(4-fluorophenylmethyl)-1H-benzimidazol-2-amine, 1.05 parts of N,N-diethylethanamine and 195 parts of dichloromethane were added dropwise 1.14 parts of methanesulfonyl chloride. Upon completion, stirring was continued for 3 hours at room temperature. Water was added and the whole was alkalized with a sodium hydroxide solution. The organic phase was separated, dried, filtered and evaporated. The residue was separated by HPLC over silica gel using a mixture of trichloromethane, hexane and methanol (45:45:10 by volume) as eluent. The first fraction was collected and the eluent was evaporated. The residue was crystallized from ac acetonitrile, yielding 1.8 parts of N-4-[2-[4-[[1-[(4-fluorophenyl)methyl]-1H-benzimidazol-2-yl]amino]-1-piperidinyl]ethyl]methanesulfonamide monohydrate; mp. 191.0° C. (compound 53).

In a similar manner there were also prepared:
N-[4-[2-[4-[[1-[(4-fluorophenyl)methyl]-1H-benzimidazol-2-yl]amino]-1-piperidinyl]ethyl]phenyl]benzenamide monohydrochloride; mp. 217.3° C. (compound 54).

N-[4-[2-[4-[[1-[(4-fluorophenyl)methyl]-1H-benzimidazol-2-yl]amino]-1-piperidinyl]ethyl]phenyl]acetamide; mp. 227.2° C. (compound 55).

EXAMPLE 41

To a stirred mixture of 4.4 parts N-[1-[2-(4-aminophenyl)ethyl]-4-piperidinyl]-1-(4-fluorophenylmethyl)-1H-benzimidazol-2-amine, 16 parts of acetic acid and 32 parts of water was added dropwise a solution of 1.2 parts of potassium isocyanate in 33 parts of water. Upon completion, stirring was continued overnight at room temperature. The reaction mixture was evaporated and the residue was taken up in water and dichloromethane. The whole was alkalized with sodium hydroxide. The precipitated product was filtered off and purified by HPLC over silica gel using a mixture of trichloromethane and methanol (90:10 by volume) as eluent. The pure fractions were collected and the eluent was evaporated. The residue was crystallized from acetonitrile, yielding 1.3 parts of N-[4-[2-[4-[[1-(4-fluorophenyl)methyl]-1H-benzimidazol-2-yl]amino]-1-piperidinyl]ethyl]phenyl]urea; mp. 186.9° C. (compound 56).

EXAMPLE 42

A mixture of 0.6 parts of isocyanatomethane, 4.43 parts of N-[1-[2-(4-aminophenyl)ethyl]-4-piperidinyl]-1-(4-fluorophenylmethyl)-1H-benzimidazol-2-amine and 135 parts of tetrahydrofuran was stirred for 3 hours at room temperature. The precipitated product was filtered off and crystallized from acetonitrile, yielding 2 parts (39.9%) of N-[4-[2-[4-[[1-[(4-fluorophenyl)methyl]-1H-benzimidazol-2-yl]amino]-1-piperidinyl]ethyl]phenyl]-N'methylurea; mp. +300° C. (compound 57).

Following the same procedure and using equivalent amounts of the appropriate starting materials, there was also prepared: N-[4-[2-[4-[[1-[(4-fluorophenyl)methyl]-1H-benzimidazol-2-yl]amino]-1-piperidinyl]ethyl]phenyl]-N'-methylthiourea monohydrate; mp. 120.2° C. (compound 58).

EXAMPLE 43

A mixture of 5 parts of N-[1-[2-(4-methoxyphenyl)ethyl]-4-piperidinyl]-1-(4-thiazolylmethyl)-1H-benzimidazol-2-amine and 150 parts of a hydrobromic acid solution 48% in water was stirred and refluxed overnight. The reaction mixture was evaporated and the solid residue was crystallized from ethanol 80%, yielding 4 parts of 4-[2-[4-[[1-(4-thiazolylmethyl)-1H-benzimidazol-2-yl]amino]-1-piperidinyl]ethyl]phenol dihydrobromide; mp. 291.0° C. (compound 59).

EXAMPLE 44

A mixture of 5 parts of N''-cyano-N-(2,2-dimethoxyethyl)-N'-[2-[4-[[1-[(4-fluorophenyl)methyl]-1H-benzimidazol-2-yl]amino]-1-piperidinyl]ethyl]guanidine and 60 parts of concentrated hydrochloric acid was stirred and refluxed for one hour. Water was added and the whole was alkalized with ammonia. The product was extracted with 4-methyl-2-pentanone. The extract was dried, filtered and evaporated. The residue was purified by column chromatography over silica gel using a mixture of trichloromethane and methanol (95:5 by volume) saturated with ammonia, as eluent. The pure fractions were collected and the eluent was evaporated. The residue was crystallized from a mixture of acetonitrile and 2,2'-oxybispropane, yielding 1 part of N-[1-[2-(2-amino-1H-imidazol-1yl]ethyl]-4-piperidinyl]-1-[(4-fluorophenyl)methyl]-1H-benzimidazol-2-amine monohydrate; mp. 171.4° C. (compound 60).

C. FORMULATIONS

The following formulations exemplify typical pharmaceutical compositions in dosage unit form suitable for systemic administration to animal and human subjects in accordance with the present invention. These examples are given to illustrate and not to limit the scope of the present invention.

"Active ingredient"(A.I.) as used throughout these examples relates to a compound of formula (I), a possible stereochemically isomeric form or pharmaceutically acceptable acid addition salt thereof.

EXAMPLE 45: ORAL DROPS

500 Grams of the A.I. was dissolved in 0.5 liters of 2-hydroxypropanoic acid and 1.5 liters of the polyethylene glycol at 60°-80° C. After cooling to 30°-40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

EXAMPLE 46: ORAL SOLUTION

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

EXAMPLE 47: CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

EXAMPLE 48: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 milliliters of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 milligrams of the active ingredient.

Coating

To a solution of 10 grams methyl cellulose in 75 milliliters of denaturated ethanol there was added a solution of 5 grms of ethyl cellulose in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109) and the whole was homogenated.

The tablet cores were coated with the thus obtained mixture in a coating apparatus.

EXAMPLE 49: INJECTABLE SOLUTION 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 propylene glycol and 4 grams of the A.I. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

EXAMPLE 50: SUPPOSITORIES

3 Grams A.I. was dissolved in a solution of 3 grams 2,3-dihydroxybutanedioic acid in 25 milliliters polyethylene glycol 400. 12 Grams surfactant and triglycerides q.s. ad 300 grams were molten together. The latter mixture was mixed well with the former solution. The thus obtained mixture was poured onto moulds at a temperature of 37°–38° C. to form 100 suppositories each containing 30 milligrams of the active ingredient.

What is claimed is:

1. A chemical compound having the formula

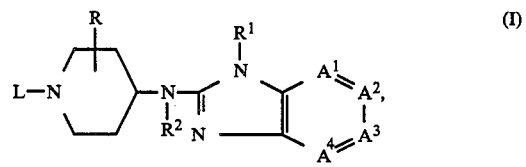

a pharmaceutically acceptable acid addition salt or a possible stereochemically isomeric form thereof, wherein:

$A^1=A^2-A^3=A^4$ is a bivalent radical having the formula

—CH=CH—CH=CH— (a-1),

—N=CH—CH=CH— (a-2),

—CH=N—CH=CH— (a-3),

—CH=CH—N=CH— (a-4), or

—CH=CH—CH=N— (a-5), wherein one or two hydrogen atoms in said radicals (a-1) - (a-5) may, each independently from each other, be replaced by halo, lower alkyl, lower alkyloxy, trifluoromethyl or hydroxy;

R is a member selected from the group consisting of hydrogen and lower alkyl;

$R^1$ is a member selected from the group consisting of hydrogen, alkyl, cycloalkyl, $Ar^1$ and lower alkyl substituted with one or two $Ar^1$ radicals;

$R^2$ is a member selected from the group consisting of hydrogen, lower alkyl, cycloalkyl, (lower alkyl)—CO—, (lower alkyloxy)—CO— and $Ar^2$-lower alkyl; and L is a radical of formula

 (b-1)

 (b-2)

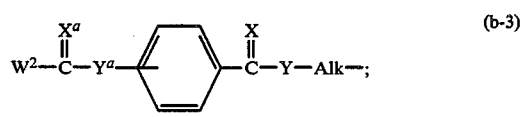 (b-3)

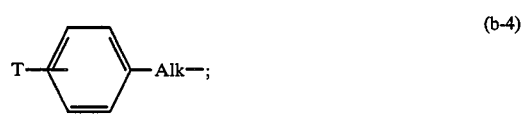 (b-4)

Het—Alk—; (b-5)

(lower alkenyl)—$Y^1$—Alk—; or (b-6)

(i) where $A^1=A^2—A^3=A^4$ is a radical of formula (a-3), (a-4) or (a-5), or (ii) where $A^1=A^2—A^3=A^4$ is a radical of formula (a-1) or (a-2), and $R^1$ is $Ar^3$ or lower alkyl substituted with one or two $Ar^3$ radicals, said $Ar^3$ being pyrazinyl, thiazolyl or imidazolyl, optionally substituted with lower alkyl:

L may also be a radical of formula:

$Ar^1$-Alk- (b-7);

said W being a member selected from the group consisting of hydrogen, lower alkyl, $Ar^1$, $Ar^1$-lower alkyl, 1-piperidinyl, 1-pyrrolidinyl, 4-morpholinyl, a radical of formula

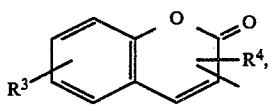 (c-1-a)

a radical of formula

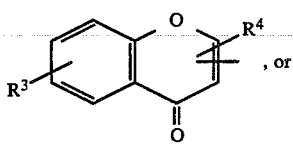 (c-1-b), or a radical of formula $W^1$-$Z^1$- (c-1-c), wherein $R^3$ and $R^4$ are each independently hydrogen or lower alkyl; and $W^1$ is cycloalkyl or lower alkyl, optionally substituted with up to two substituents selected from the group consisting of hydroxy, lower alkyloxy, 1-piperidinyl, 1-pyrrolidinyl, 4-morpholinyl and $Ar^1$; and where $Z^1$ is $Nr^8$, $W^1$ may also be hydrogen, amino, lower alkylamino, $Ar^1$-amino or nitro;

said $W^2$ being a member selected from the group consisting of hydrogen, lower alkyl, $Ar^1$ and a radical of formula:

$R^5$-$Z^1$- (c-2-a), wherein $R^5$ is hydrogen, lower alkyl or $Ar^1$;
said T being a radical of formula:

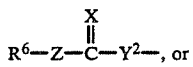 (c-3-a)

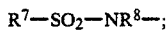 (c-3-b);

$R^6$ being hydrogen, lower alkyl or $Ar^1$;
$R^7$ being lower alkyl or $Ar^1$; and
$R^8$ being hydrogen or lower alkyl;
said Het being a radical of formula (c-4-a), (c-4-b), or a radical of formula

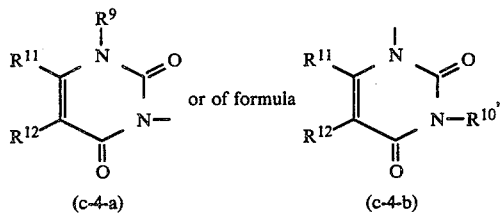

wherein $R^9$, $R^{10}$, $R^{11}$ and $R^{12}$ are each independently hydrogen or lower alkyl; or a radical of formula

 (c-4-c)

wherein $R^{13}$ is hydrogen, lower alkyl or amino, or said Het being furan substituted with lower alkyl, said lower alkyl being optionally substituted with hydroxy, mercapto, lower alkyloxy, lower alkylthio, (aminolower alkyl)thio, $Ar^1$—O— or a radical of formula

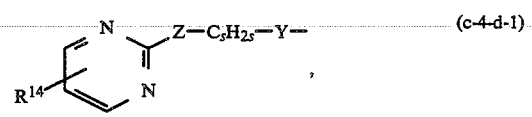 (c-4-d-1)

s being an integer of from 1 to 6 inclusive; or where Z or Y is a direct bond, s may also be 0; and $R^{14}$ being hydrogen or lower alkyl;
wherein:
n is 0 or the integer 1 or 2;
X is O, S, $NR^{15}$ or $CHNO_2$;
Y is O, S, $NR^{16}$ or a direct bond;
$Y^1$ is O, S or $NR^{16}$;
$Y^2$ is S or $NR^{16}$;
Z is O, S, $NR^8$ or a direct bond;
$Z^1$ is O, S or $NR^8$;
$X^a$ and $Y^a$ independently having the same meaning of X respectively Y;
said $R^{15}$ being hydrogen, lower alkyl, cyano, nitro, $Ar^2$-sulfonyl, lower alkylsulfonyl, lower alkylcarbonyl or $Ar^2$-carbonyl;
said $R^{16}$ being hydrogen, lower alkyl, ($Ar^2$)lower alkyl, 2-lower alkyloxy-1,2-dioxoethyl; or a radical of formula —C(=X)—$R^{17}$; $R^{17}$ being hydrogen, lower alkyl, $Ar^2$, $Ar^2$-lower alkyl, lower alkyloxy, $Ar^2$-lower alkyloxy, mono- or di(lower alkyl)amino, $Ar^2$-lower alkylamino or $Ar^2$-lower alkyl(lower alkyl)amino;
provided that:
(i) when $A^1=A^2—A^3=A^4$ is a radical of formula (a-1) or (a-2), and L is a radical of formula (b-1), wherein W is other than hydrogen or other than a radical of formula (c-1-a) or (c-1-b), then X is other than O;
(ii) when L is a radical of formula (b-1), wherein W is a radical of formula (c-1-c), wherein $Z^1$ is NH then $W^1$ is other than hydrogen or lower alkyl;
(iii) when $A^1=A^2—A^3=A^4$ is a radical of formula (a-1) or (a-2), and L is a radical of formula (b-3), wherein X is O, Y is NR$^{16}$, O or a direct bond, and X$^a$ is O,
(a) then Y$^a$ is not O;
(b) and W$^2$ being lower alkyl then Y$^a$ is not a direct bond;

wherein Ar$^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and lower alkyl-CO-; thienyl; halothienyl; furanyl; lower alkyl substituted furanyl; pyridinyl; pyrazinyl; thiazolyl and midazolyl optionally substituted with lower alkyl; and wherein Ar$^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)-CO.

2. A chemical compound according to claim 1, wherein L is a radical of formula (b-1), wherein Y is NH, X is O and W is hydrogen; or L is a radical of formula (b-1) wherein X is S, NH or NCN, Y is NH and W is 1-piperidinyl, 1-pyrrolidinyl, 4-morpholinyl, or a radical of formula (c-1-c), wherein Z$^1$ is NR$^8$ and W$^1$ is amino, nitro or lower alkyl, optionally substituted with one hydroxy, lower alkyloxy, 1-piperidinyl, 1-pyrrolidinyl, 4-morpholinyl or phenyl radical, or with two lower alkyloxy radicals; or L is a radical of formula (b-1), wherein X is S, NH or NCN, Y is NH and W is lower alkyloxy or lower alkylthio; or wherein L is a radical or formula (b-1) wherein W is a radical of formula (c-1-a) or (c-1-b); or L is a radical of formula (b-2) wherein n is 1, X is O or S and W is a radical of formula (c-1-c), wherein Z$^1$ is NR$^8$ and W$^1$ is lower alkyl; or L is a radical of formula (b-3), wherein X is O, Y is NH, X$^a$ is O, Y$^a$ is NR$^{15}$ and W$^2$ is lower alkyl; or L is a radical of formula (b-4), wherein T is a radical of formula (c-3-a), wherein X is O or S, Z is NR$^8$ and R$^6$ is hydrogen or lower alkyl; or wherein T is a radical of formula (c-3-b), wherein R$^8$ is hydrogen and R$^7$ is lower alkyl; or L is a radical of formula (b-5) wherein Het is a radical of formula (c-4-a), wherein R$^9$, R$^{11}$ and R$^{12}$ are hydrogen; or wherein Het is a radical of formula (c-4-c); or wherein Het is furan substituted with lower alkyl being substituted with hydroxy or with a radical of formula (c-4-d-1), wherein Y is O or S, Z is NH or a direct bond and R$^{14}$ is hydrogen; or L is a radical of formula (b-6) wherein Y$^1$ is O; or L is a radical of formula (b-7) wherein Ar$^1$ is phenyl substituted with hydroxy or lower alkyloxy.

3. An anti-allergic composition comprising an inert carrier and an anti-allergic effective amount of a compound having the formula

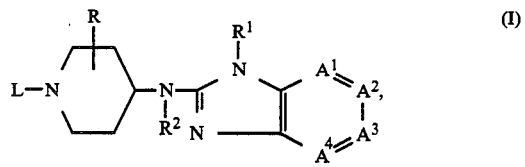

a pharmaceutically acceptable acid addition salt or a possible stereochemically isomeric form thereof, wherein:

A$^1$=A$^2$—A$^3$=A$^4$ is a bivalent radical having the formula

—CH=CH—CH=CH—(a-1),

—N=CH—CH=CH—(a-2),

—CH=N—CH=CH—(a-3),

—CH=CH—N=CH—(a-4), or

—CH=CH—CH=N—(a-5), wherein one or two hydrogen atoms in said radicals (a-1)–(a-5) may, each independently from each other, be replaced by halo, lower alkyl, lower alkyloxy, trifluoromethyl or hydroxy;

R is a member selected from the group consisting of hydrogen and lower alkyl;

R$^1$ is a member selected from the group consisting of hydrogen, alkyl, cycloalkyl, Ar$^1$ and lower alkyl substituted with one or two Ar$^1$ radicals;

R$^2$ is a member selected from the group consisting of hydrogen, lower alkyl, cycloalkyl, (lower alkyl)—CO—, (lower alkyloxy)—CO— and Ar$^2$-lower alkyl; and L is a radical of formula

 (b-1)

 (b-2)

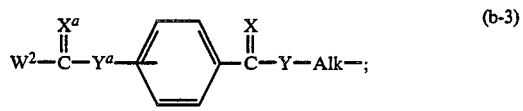 (b-3)

 (b-4)

Het—Alk—; (b-5)

(lower alkenyl)—Y$^1$—Alk—; or (b-6)

(i) where A$^1$=A$^2$—A$^3$=A$^4$ is a radical of formula (a-3), (a-4) or (a-5), or
(ii) where A$^1$=A$^2$—A$^3$=A$^4$ is a radical of formula (a-1) or (a-2), and R$^1$ is Ar$^3$ or lower alkyl substituted with one or two Ar$^3$ radicals, said Ar$^3$ being pyrazinyl, thiazolyl or imidazolyl, optionally substituted with lower alkyl:

L may also be a radical of formula:

Ar$^1$—Alk—(b-7);

said W being a member selected from the group consisting of hydrogen, lower alkyl, Ar$^1$, Ar$^1$-lower alkyl, 1-piperidinyl, 1-pyrrolidinyl, 4-morpholinyl, a radical of formula

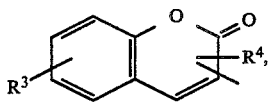 (c-1-a)

a radical of formula

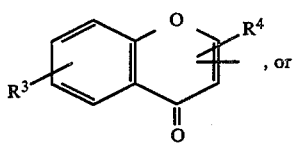 (c-1-b), or a radical of formula

W$^1$—Z$^1$—(c-1-c), wherein R$^3$ and R$^4$ are each independently hydrogen or lower alkyl; and W$^1$ is cycloalkyl or lower alkyl, optionally substituted with up to two substituents selected from the group consisting of hydroxy, lower alkyloxy, 1-piperidinyl, 1-pyrrolidinyl, 4-morpholinyl and Ar$^1$; and where Z$^1$ is NR$^8$, W$^1$ may also be hydrogen, amino, lower alkylamino, Ar$^1$-amino or nitro;

said W$^2$ being a member selected from the group consisting of hydrogen, lower alkyl, Ar$^1$ and a radical of formula:

R$^5$-Z$^1$—(c-2-a), wherein R$^5$ is hydrogen, lower alkyl or Ar$^1$;
said T being a radical of formula:

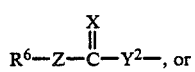 (c-3-a)

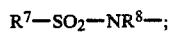 (c-3-b)

R$^6$ being hydrogen, lower alkyl or Ar$^1$;
R$^7$ being lower alkyl or Ar$^1$; and
R$^8$ being hydrogen or lower alkyl;
said Het being a radical of formula (c-1-a), (c-1-b), or a radical of formula

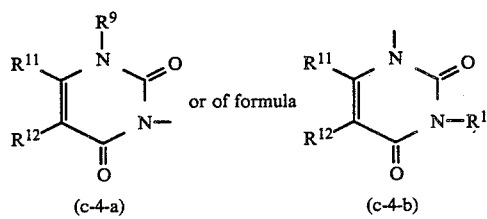

wherein R$^9$, R$^{10}$, R$^{11}$ and R$^{12}$ are each independently hydrogen or lower alkyl; or a radical of formula

 (c-4-c)

wherein R$^{13}$ is hydrogen, lower alkyl or amino, or
said Het being furan substituted with lower alkyl, said lower alkyl being optionally substituted with hydroxy, mercapto, lower alkyloxy, lower alkylthio, (aminolower alkyl)thio, Ar$^1$-O- or a radical of formula

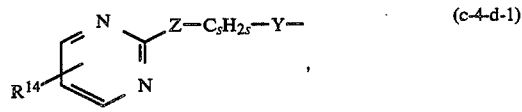 (c-4-d-1)

s being an integer of from 1 to 6 inclusive; or where Z or Y is a direct bond, s may also be 0; and R$^{14}$ being hydrogen or lower alkyl;
wherein:
n is 0 or the integer 1 or 2;
X is O, S, NR$^{15}$ or CHNO$_2$;
Y is O, S, NR$^{16}$ or a direct bond;
Y$^1$ is O, S or NR$^{16}$;
Y$^2$ is S or NR$^{16}$;
Z is O, S, NR$^8$ or a direct bond;
Z$^1$ is O, S or NR$^8$;
X$^a$ and Y$^a$ independently having the same meaning of X respectively Y;
said R$^{15}$ being hydrogen, lower alkyl, cyano, nitro, Ar$^2$-sulfonyl, lower alkylsulfonyl, lower alkylcarbonyl or Ar$^2$-carbonyl;
said R$^{16}$ being hydrogen, lower alkyl, (Ar$^2$)lower alkyl, 2-lower alkyloxy-1,2-dioxoethyl; or a radical of formula —C(=X)-R$^{17}$; R$^{17}$ being hydrogen, lower alkyl, Ar$^2$, Ar$^2$-lower alkyl, lower alkyloxy, Ar$^2$-lower alkyloxy, mono- or di(lower alkyl)amino, Ar$^2$-lower alkylamino or Ar$^2$-lower alkyl(lower alkyl)amino;
provided that:
(i) when A$^1$=A$^2$—A$^3$=A$^4$ is a radical of formula (a-1) or (a-2), and L is a radical of formula (b-1), wherein W is other than hydrogen or other than a radical of formula (c-1-a) or (c-1-b), then X is other than O;
(ii) when L is a radical of formula (b-1), wherein W is a radical of formula (c-1-c), wherein Z$^1$ is NH when W$^1$ is other than hydrogen or lower alkyl;
(iii) when A$^1$=A$^2$—A$^3$=A$^4$ is a radical of formula (a-1) or (a-2), and L is a radical of formula (b-3), wherein X is O, Y is NR$^{16}$, O or a direct bond, and X$^a$ is O,
(a) then Y$^a$ is not O;
(b) and W$^2$ being lower alkyl then Y$^a$ is not a direct bond;
wherein Ar$^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and lower alkyl—CO—; thienyl; halothienyl; furanyl; lower alkyl substituted furanyl; pyridinyl; pyrazinyl; thiazolyl and imidazolyl optionally substituted with lower alkyl; and wherein $Ar^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)-CO.

4. A composition according to claim 3 wherein L is a radical of formula (b-1), wherein Y is NH, X is O and W is hydrogen; or L is a radical of formula (b-1) wherein X is S, NH or NCN, Y is NH and W is 1-piperidinyl, 1-pyrrolidinyl, 4-morpholinyl, or a radical of formula (c-1-c), wherein $Z^1$ is $NR^8$ and $W^1$ is amino, nitro or lower alkyl, optionally substituted wth one hydroxy, lower alkyloxy, 1-piperidinyl, 1-pyrrolidinyl, 4-morpholinyl or phenyl radical, or with two lower alkyloxy radicals; or L is a radical of formula (b-1), wherein X is S, NH of NCN, Y is NH and W is lower alkyloxy or lower alkylthio; or wherein L is a radical of formula (b-1) wherein W is a radical of formula (c-1-a) or (c-1-b); or L is a radical of formula (b-2) wherein n is 1, X is O or S and W is a radical of formula (c-1-c), wherein $Z^1$ is $NR^8$ and $W^1$ is lower alkyl; or L is a radical of formula (b-3), wherein X is O, Y is NH, $X^a$ is O, $Y^a$ is $NR^{15}$ and $W^2$ is lower alkyl; or L is a radical of formula (b-4), wherein T is a radical of formula (c-3-a), wherein X is O or S, Z is $NR^8$ and $R^6$ is hydrogen or lower alkyl; or wherein T is a radical of formula (c-3-b), wherein $R^8$ is hydrogen and $R^7$ is lower alkyl; or L is a radical of formula (b-5) wherein Het is a radical of formula (c-4-a), wherein $R^9$, $R^{11}$ and $R^{12}$ are hydrogen; or wherein Het is a radical of formula (c-4-c); or wherein Het is furan substituted with lower alkyl being substituted with hydroxy or with a radical of formula (c-4-d-1), wherein Y is O or S, Z is NH or a direct bond and $R^{14}$ is hydrogen; or L is a radical of formula (b-6) wherein $Y^1$ is O; or L is a radical of formula (b-7) wherein $Ar^1$ is phenyl substituted with hydroxy or lower alkyloxy.

5. A method of treating allergic diseases in warm-blooded animals suffering from same which method comprises the systemic administration to warm-blooded animals of an effective anti-allergic amount of a compound having the formula

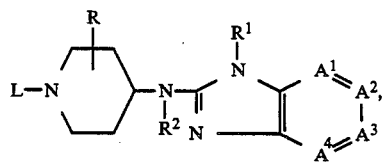
(I)

a pharmaceutically acceptable acid addition salt or a possible stereochemically isomeric form thereof, wherein:

$A^1=A^2—A^3=A^4$ is a bivalent radical having the formula

—CH=CH—CH=CH— (a-1),

—N=CH—CH=CH— (a-2),

—CH=N—CH=CH— (a-3),

—CH=CH—N=CH— (a-4), or

—CH=CH—CH=N— (a-5), wherein one or two hydrogen atoms in said radicals (a-1)–(a-5) may, each independently from each other, be replaced by halo, lower alkyl, lower alkyloxy, trifluoromethyl or hydroxy;

R is a member selected from the group consisting of hydrogen and lower alkyl;

$R^1$ is a member selected from the group consisting of hydrogen, alkyl, cycloalkyl, $Ar^1$ and lower alkyl substituted with one or two $Ar^1$ radicals;

$R^2$ is a member selected from the group consisting of hydrogen, lower alkyl, cycloalkyl (lower alkyl)—CO—, (lower alkyloxy)—CO— and $Ar^2$-lower alkyl; and L is a radical of formula

 (b-1)

 (b-2)

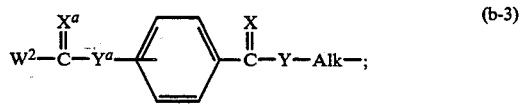 (b-3)

 (b-4)

Het—Alk—; (b-5)

(lower alkenyl)—$Y^1$—Alk—; or (b-6)

(i) where $A^1=A^2—A^3=A^4$ is a radical of formula (a-3), (a-4) or (a-5), or (ii) where $A^1=A^2—A^3=A^4$ is a radical of formula (a-1) or (a-2), and $R^1$ is $Ar^3$ or lower alkyl substituted with one or two $Ar^3$ radicals, said $Ar^3$ being pyrazinyl, thiazolyl or imidazolyl, optionally substituted with lower alkyl;

L may also be a radical of formula:

$Ar^1$—Alk— (b-7);

said W being a member selected from the group consisting of hydrogen, lower alkyl, $Ar^1$, $Ar^1$-lower alkyl, 1-piperidinyl, 1-pyrrolidinyl, 4-morpholinyl, a radical of formula

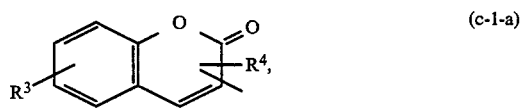 (c-1-a)

a radical of formula

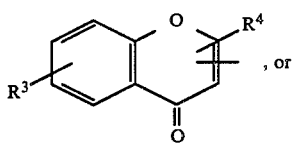 (c-1-b)

a radical of formula $W^1\text{-}Z^1\text{—}$ (c-1-c), wherein $R^3$ and $R^4$ are each independently hydrogen or lower alkyl; and $W^1$ is cycloalkyl or lower alkyl, optionally substituted with up to two substituents selected from the group consisting of hydroxy, lower alkyloxy, 1-piperidinyl, 1-pyrrolidinyl, 4-morpholinyl and $Ar^1$; and where $Z^1$ is $NR^8$, $W^1$ may also be hydrogen, amino, lower alkylamino, $Ar^1$-amino or nitro;

said $W^2$ being a member selected from the group consisting of hydrogen, lower alkyl, $Ar^1$ and a radical of formula:

$R^5\text{-}Z^1\text{—}$ (c-2-a), wherein $R^5$ is hydrogen, lower alkyl or $Ar^1$;
said T being a radical of formula:

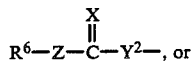 (c-3-a)

$R^7\text{—}SO_2\text{—}NR^8\text{—}$; (c-3-b)

$R^6$ being hydrogen, lower alkyl or $Ar^1$;
$R^7$ being lower alkyl or $Ar^1$; and
$R^8$ being hydrogen or lower alkyl;
said Het being a radical of formula (c-1-a), (c-1-b), or a radical of formula

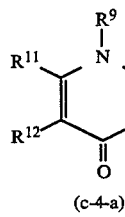 or of formula 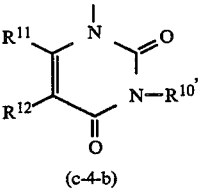

(c-4-a)  (c-4-b)

wherein $R^9$, $R^{10}$, $R^{11}$ and $R^{12}$ are each independently hydrogen or lower alkyl; or a radical of formula

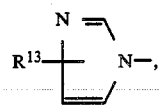 (c-4-c)

wherein $R^{13}$ is hydrogen, lower alkyl or amino, or
said Het being furan substituted with lower alkyl, said lower alkyl being optionally substituted with hydroxy, mercapto, lower alkyloxy, lower alkylthio, (aminolower alkyl)thio, $Ar^1$-O— or a radical of formula

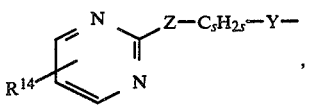 (c-4-d-1)

s being an integer of from 1 to 6 inclusive; or where Z or Y is a direct bond, s may also be 0; and $R^{14}$ being hydrogen or lower alkyl;
wherein:
n is 0 or the integer 1 or 2;
X is O, S, $NR^{15}$ or $CHNO_2$;
Y is O, S, $NR^{16}$ or a direct bond;
$Y^1$ is O, S or $NR^{16}$;
$Y^2$ is S or $NR^{16}$;
Z is O, S, $NR^8$ or a direct bond;
$Z^1$ is O, S or $NR^8$;
$X^a$ and $Y^a$ independently having the same meaning of X respectively Y;
said $R^{15}$ being hydrogen, lower alkyl, cyano, nitro, $Ar^2$-sulfonyl, lower alkylsulfonyl, lower alkylcarbonyl or $Ar^2$-carbonyl;
said $R^{16}$ being hydrogen, lower alkyl, $(Ar^2)$lower alkyl, 2-lower alkyloxy-1,2-dioxoethyl; or a radical of formula —C(=X)-$R^{17}$; $R^{17}$ being hydrogen, lower alkyl, $Ar^2$, $Ar^2$-lower alkyl, lower alkyloxy, $Ar^2$-lower alkyloxy, mono- or di(lower alkyl)amino, $Ar^2$-lower alkylamino or $Ar^2$-lower alkyl(lower alkyl)amino;
provided that:
(i) when $A^1=A^2\text{—}A^3=A^4$ is a radical of formula (a-1) or (a-2), and L is a radical of formula (b-1), wherein W is other than hydrogen or other than a radical of formula (c-1-a) or (c-1-b), then X is other than O;
(ii) when L is a radical of formula (b-1), wherein W is a radical of formula (c-1-c), wherein $Z^1$ is NH then $W^1$ is other than hydrogen or lower alkyl;
(iii) when $A^1=A^2\text{—}A^3=A^4$ is a radical of formula (a-1) or (a-2), and L is a radical of formula (b-3), wherein X is O, Y is $NR^{16}$, O or a direct bond, and $X^a$ is O,
(a) then $Y^a$ is not O;
(b) and $W^2$ being lower alkyl then $Y^a$ is not a direct bond;
wherein $Ar^1$ is a member selected from the group consisting of phenyl, being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and lower alkyl-CO—; thienyl; halothienyl; furanyl; lower alkyl substituted furanyl; pyridinyl; pyrazinyl; thiazolyl and imidazolyl optionally substituted with lower alkyl; and wherein $Ar^2$ is a member selected from the group consisting of phenyl being optionally substituted with up to three substituents each independently selected from the group consisting of halo, hydroxy, nitro, cyano, trifluoromethyl, lower alkyl, lower alkyloxy, lower alkylthio, mercapto, amino, mono- and di(lower alkyl)amino, carboxyl, lower alkyloxycarbonyl and (lower alkyl)-CO.

6. A method according to claim 3 wherein L is a radical of formula (b-1), wherein Y is NH, X is O and W is hydrogen; or L is a radical of formula (b-1) wherein X is S, NH ior NCN, Y is NH and W is 1-piperidinyl, 1-pyrrolidinyl, 4-morpholinyl, or a radical of formula (c-1-c), wherein $Z^1$ is $NR^8$ and $W^1$ is amino, nitro or lower alkyl, optionally substituted with one hydroxy, lower alkyloxy, 1-piperidinyl, 1-pyrrolidinyl, 4-morpholinyl or phenyl radical, or with two lower alkyloxy radicals; or L is a radical formula (b-1), wherein X is S, NH or NCN, Y is NH and W is lower alkyloxy or lower alkylthio; or wherein L is a radical of formula (b-1) wherein W is a radical of formula (c-1-a) or (c-1-b); or L is a radical of formula (b-2) wherein n is 1, X is O or S and W is a radical of formula (c-1-c), wherein $Z^1$ is $NR^8$ and $W^1$ is lower alkyl; or L is a radical of formula (b-3), wherein X is O, Y is NH, $X^a$ is O, $Y^a$ is $NR^{15}$ and $W^2$ is lower alkyl; or L is a radical of formula (b-4), wherein T is a radical of formula (c-3-a), wherein X is O or S, Z is $NR^8$ and $R^6$ is hydrogen or lower alkyl; or wherein T is a radical of formula (c-3-b), wherein $R^8$ is hydrogen and $R^7$ is lower alkyl; or L is a radical of formula (b-5) wherein Het is a radical of formula (c-4-a), wherein $R^9$, $R^{11}$ and $R^{12}$ are hydrogen; or wherein Het is a radical of formula (c-4-c); or wherein Het is furan substituted with lower alkyl being substituted with hydroxy or with a radical of formula (c-4-d-1), wherein Y is O or S, Z is NH or a direct bond and $R^{14}$ is hydrogen; or L is a radical of formula (b-6) wherein $Y^1$ is O; or L is a radical of formula (b-7) wherein $Ar^1$ is phenyl substituted with hydroxy or lower alkyloxy.

7. A chemical compound according to claim 1 wherein $R^1$ is lower alkyl substituted with one $Ar^1$ radical.

8. A composition according to claim 3 wherein $R^1$ is lower alkyl substituted with one $Ar^1$ radical.

9. A method according to claim 5 wherein $R^1$ is lower alkyl substituted with one $Ar^1$ radical.

* * * * *